US012527562B2

(12) United States Patent
Theofilos et al.

(10) Patent No.: US 12,527,562 B2
(45) Date of Patent: Jan. 20, 2026

(54) NERVE RETRACTOR TOOL

(71) Applicant: SNJ Patents, LLC, Palm Beach Gardens, FL (US)

(72) Inventors: Charles S. Theofilos, Palm Beach Gardens, FL (US); Stefan C. Theofilos, Palm Beach Gardens, FL (US); Krutik Chaten Shah, Fulham (GB)

(73) Assignee: SNJ Patents, LLC, Palm Beach Gardens, FL (US)

(*) Notice: Subject to any disclaimer, the term of this patent is extended or adjusted under 35 U.S.C. 154(b) by 497 days.

(21) Appl. No.: 17/954,140

(22) Filed: Sep. 27, 2022

(65) Prior Publication Data

US 2023/0016652 A1 Jan. 19, 2023

Related U.S. Application Data

(63) Continuation-in-part of application No. 16/751,680, filed on Jan. 24, 2020, now Pat. No. 11,759,192.

(60) Provisional application No. 63/226,469, filed on Jul. 28, 2021.

(51) Int. Cl.
*A61B 17/02* (2006.01)
*A61B 17/00* (2006.01)

(52) U.S. Cl.
CPC .... *A61B 17/02* (2013.01); *A61B 2017/00407* (2013.01)

(58) Field of Classification Search
CPC ... A71B 17/02; A71B 17/0206; A71B 17/025; A61B 90/50
See application file for complete search history.

(56) References Cited

U.S. PATENT DOCUMENTS

| | | | | |
|---|---|---|---|---|
| 5,123,403 | A | 6/1992 | Lavyne | |
| 6,007,487 | A | 12/1999 | Foley et al. | |
| 7,226,413 | B2 | 6/2007 | McKinley | |
| D621,041 | S | 8/2010 | Mao et al. | |
| 9,510,812 | B2 * | 12/2016 | Brown | A61B 17/02 |
| 2004/0143165 | A1 | 7/2004 | Alleyne | |
| 2007/0027363 | A1 | 2/2007 | Gannoe et al. | |
| 2008/0221394 | A1 | 9/2008 | Melkent et al. | |
| 2010/0256454 | A1 | 10/2010 | Farley et al. | |

(Continued)

FOREIGN PATENT DOCUMENTS

| | | |
|---|---|---|
| CN | 210811237 | 6/2020 |
| CN | 211911682 | 11/2020 |

(Continued)

*Primary Examiner* — Christopher J Beccia
(74) *Attorney, Agent, or Firm* — McHale & Slavin, P.A.

(57) ABSTRACT

A retractor, preferably a nerve root retractor, comprising three components: an upper portion, a mid-portion, and a lower portion. The nerve retractor is designed to eliminate the requirement of having a person hold the retractor tool during a surgical procedure. The nerve retractor can be secured to a portion of the anatomical structure involved with, or near, the surgical procedure site, and utilizes an actuating device which allows the user to manipulate the angle of orientation of the arm portion or anatomical structure retractor portion. The anatomical structure retractor may comprise a modular anatomical structure engaging member/head, allowing the surgeon to use multiple or differently configured structure engaging members/heads during a procedure as needed.

11 Claims, 38 Drawing Sheets

(56) References Cited

U.S. PATENT DOCUMENTS

| | | | | |
|---|---|---|---|---|
| 2015/0182211 | A1* | 7/2015 | Nowak | A61B 17/0206 600/215 |
| 2016/0242757 | A1 | 8/2016 | Cryder et al. | |
| 2016/0354073 | A1 | 12/2016 | Nel et al. | |
| 2018/0353258 | A1 | 12/2018 | Traub et al. | |
| 2019/0015089 | A1 | 1/2019 | Rosenbaum et al. | |
| 2021/0228196 | A1 | 7/2021 | Theofilos et al. | |
| 2022/0240915 | A1* | 8/2022 | Farley | A61B 17/02 |

FOREIGN PATENT DOCUMENTS

| | | |
|---|---|---|
| CN | 213552012 | 6/2021 |
| WO | WO2019055173 | 3/2019 |

* cited by examiner

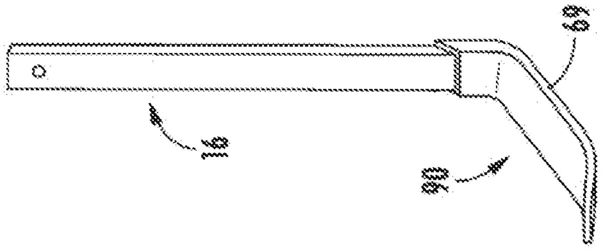
FIG. 14H
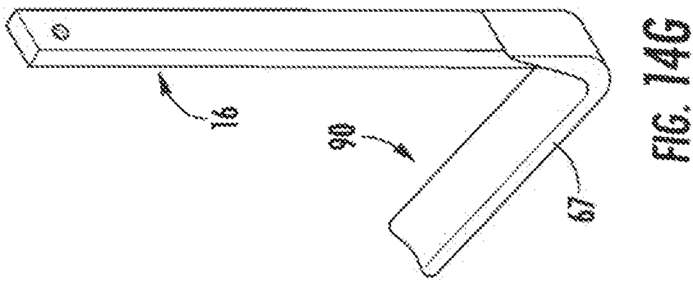
FIG. 14G
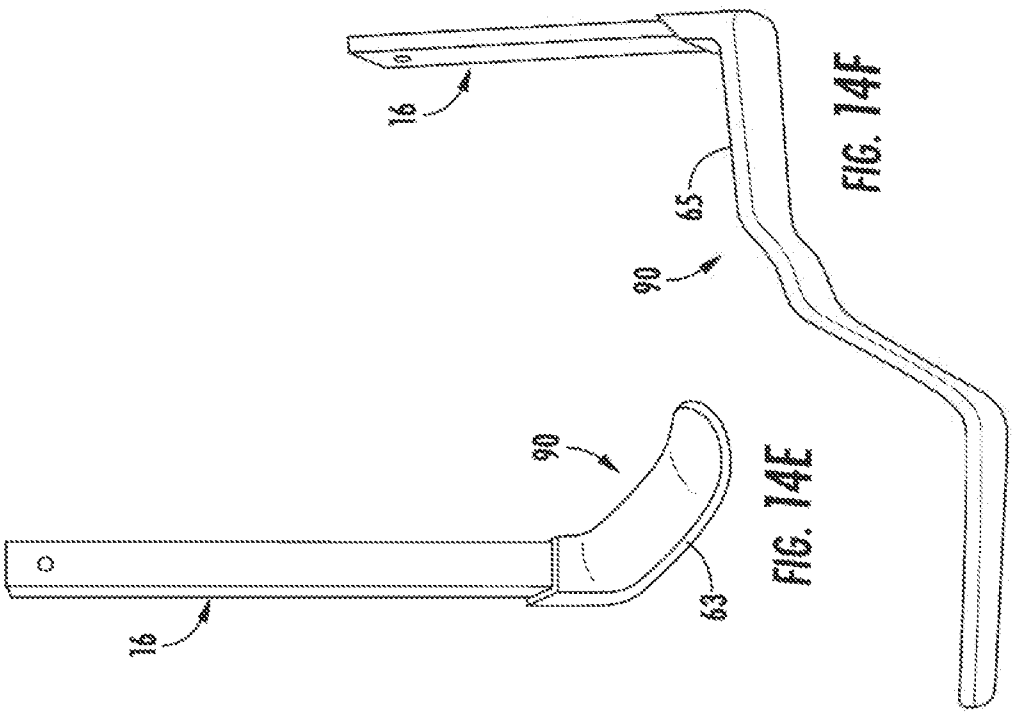
FIG. 14F
FIG. 14E
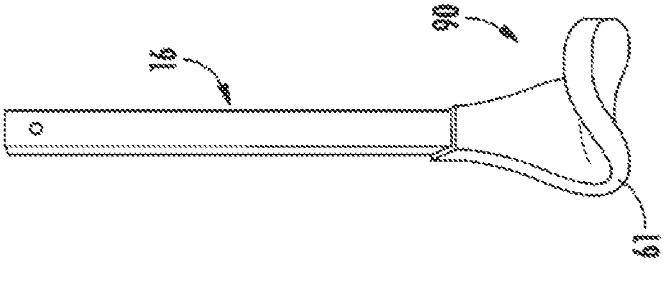
FIG. 14D

NERVE RETRACTOR TOOL

CROSS-REFERENCE TO RELATED APPLICATIONS

This application claims priority to U.S. Provisional Application No. 63/226,469, filed on Jul. 28, 2021, entitled "NERVE RETRACTOR TOOL." This application is also a continuation-in-part of U.S. application Ser. No. 16/751,680 filed Jan. 24, 2020, entitled "NERVE RETRACTOR TOOL," published as U.S. Publication No. US2021/0228196 A1 on Jul. 29, 2021. All the applications, publications and patents listed in this paragraph are incorporated herein by reference in their entirety as examples.

FIELD OF THE INVENTION

The present invention relates to medical devices; to medical devices that are used in surgical procedures, such as neurosurgical or orthopedic surgeries; and more particularly, to a retractor, particularly to a nerve root retractor which eliminates the need for a secondary person to hold the retractor tool during a surgery.

BACKGROUND OF THE INVENTION

Often times in surgical procedures, the surgeon requires clear views of the operating field to ensure the surgical procedure is done properly and minimize the risk of complications. It is imperative that the surgeon creates and maintains a surgical field large enough to enable the surgeon to view the surgical area and perform the necessary work within the treatment zone without damaging surrounding tissues. Typically, a retractor is used to clear the field of obstructing tissues or organs. In the case of spinal surgeries, allowing neurosurgeons to access various portions of the spine, such as the lumbar portion of the spine, retractors, such as a nerve root retractor, assists the surgeon by providing a tool designed to hold back the nerve root covering the vertebrae and disks.

The nerve root is the segment of a nerve leaving the central nervous system. The spinal nerve carries sensory, motor, and automatic signals between the spinal cord and the body. There are two sections of the nerve root: the cervical spine nerve roots, which are located in the neck, and the lumbar spine nerve roots, which are located in the lower back. Nerve roots are very susceptible to damage during surgical procedures, and such damage must be avoided. Damage to the nerve root can lead to paralysis to the affected muscle. During spinal surgery, the surgeon or assistant has to retract the nerve root because it blocks the surgeon's path to the vertebrae and discs.

Current methods utilizing nerve root retractors during surgical procedures require utilizing a surgical first assistant to retract the nerve root and spinal sac. The surgical first assistant is responsible for holding the nerve root and spinal sac in place while the surgeon operates. This arrangement can be problematic because the assistant may be unable to visualize what is happening in a deep wound. In addition, fatigue can set in due to a lengthy procedure, increasing the risk of the assistant's hand becoming unsteady. If this occurs, the nerve retractor held by the surgical first assistant has a greater likelihood of moving. Such movement increases the risk of vital nerve damage, ultimately resulting in permanent damage and paralysis in the patient.

SUMMARY OF THE INVENTION

The present invention relates to a retractor, particularly a nerve retractor, designed to allow a user, such as a surgeon, to steadily retract a spinal sac and nerve root traveling through the spinal canal. The nerve retractor is designed to provide the user with an easier and safer tool to access the surgical target, allowing the surgeon to work without damaging vital neural structures. The nerve retractor is designed to eliminate the requirement of having an independent member hold the retractor tool, thus providing a safer procedure. In addition, the nerve retractor connects to the spine. Accordingly, unlike a human holding a retractor, if any movement of the patient occurs, the nerve retractor is steady and will not change its position. Preferably, the nerve retractor comprises three components: a base portion, an arm portion, and an anatomical structure retractor portion. The nerve retractor can be secured to a portion of the anatomical structure involved with, or near, the surgical procedure site. The nerve retractor utilizes an actuating device which allows the user to manipulate the angle of orientation of the arm portion or anatomical structure retractor portion. The anatomical structure retractor may comprise a modular anatomical structure engaging member/head, allowing the surgeon to use multiple or differently configured structure engaging members/heads during a procedure as needed.

Accordingly, it is an objective of the invention to provide a medical device for use in surgical procedures.

It is a further objective of the invention to provide a medical device for use in spinal procedures.

It is yet another objective of the invention to provide a medical device for use in various medical procedures.

It is a further objective of the invention to provide a nerve retractor.

It is yet another objective of the invention to provide a nerve retractor designed to allow a user, such as a surgeon or assistant, to steadily retract a spinal sac and nerve root.

It is a still further objective of the invention to provide a nerve retractor designed to be secured to a portion of the anatomical structure involved with or near the surgical procedure.

It is a still further objective of the invention to provide a nerve retractor that utilizes an actuating device which allows the user to manipulate the angle of orientation of the arm portion or anatomical structure retractor portion.

It is a further objective of the invention to provide a nerve retractor having a modular anatomical structure engaging member/head.

It is yet another objective of the invention to provide a nerve retractor having a modular anatomical structure engaging member/head, allowing the surgeon to use multiple or differently configured structure engaging members/heads during a procedure as needed.

It is a still further objective of the invention to provide a kit having one or more components of a nerve retractor.

It is a further objective of the invention to provide a kit having one or more modular anatomical structure engaging members/heads.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 14D is a perspective view of the retractor portion of the nerve retractor illustrated in FIG. 14A, shown with a curved blade modular head unit;

FIG. 14E is a perspective view of the retractor portion of the nerve retractor illustrated in FIG. 14A, shown with an alternative curved blade modular head unit;

FIG. 14F is a perspective view of the retractor portion of the nerve retractor illustrated in FIG. 14A, shown with a bayonet modular head unit;

FIG. 14G is a perspective view of the retractor portion of the nerve retractor illustrated in FIG. 14A, shown with a paddle shaped modular head unit;

FIG. 14H is a perspective view of the retractor portion of the nerve retractor illustrated in FIG. 14A, shown with an alternative curved modular head unit;

DETAILED DESCRIPTION OF THE INVENTION

Figure 1B:
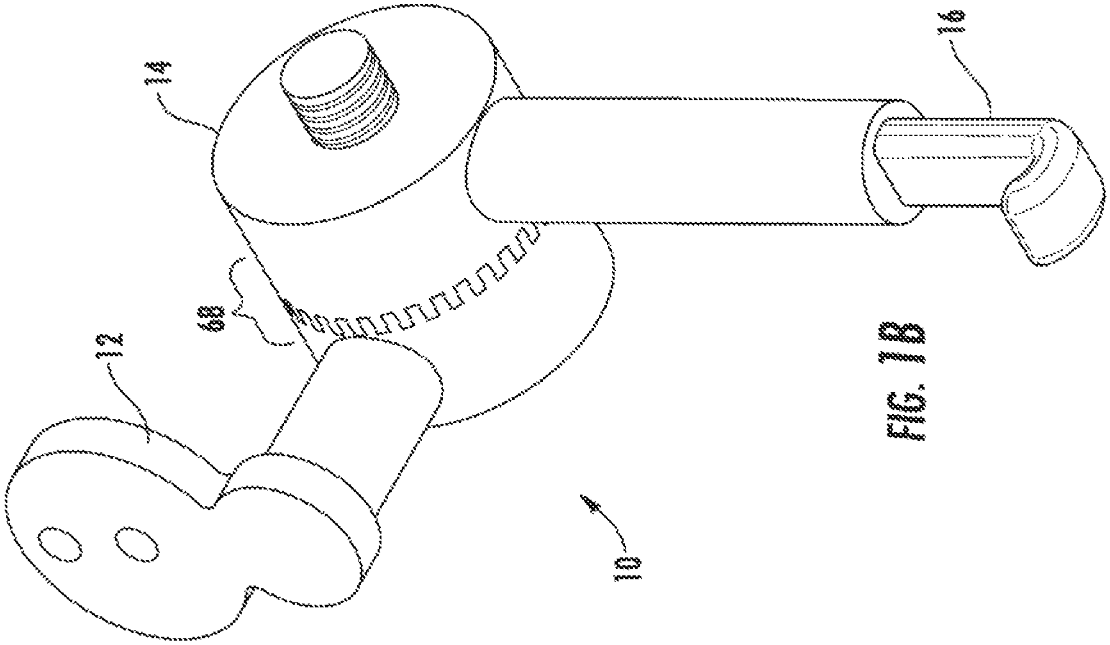
FIG. 1B is a perspective view of the nerve retractor with a non-angled post and main body orientation.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 1A:
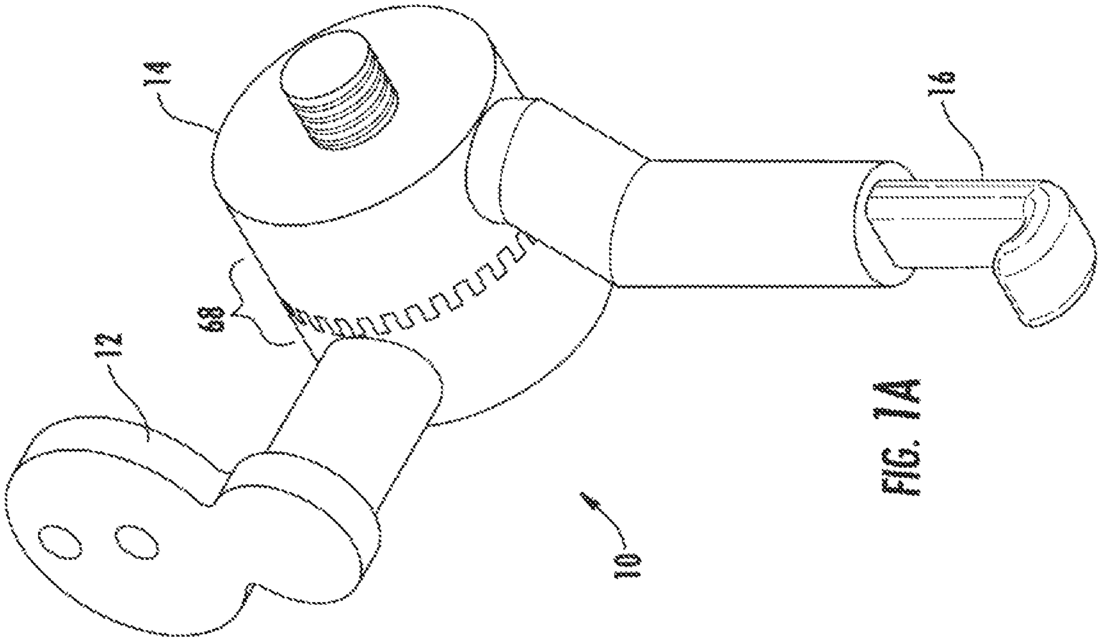
FIG. 1A is a perspective view of an illustrative embodiment of a nerve retractor.
Figure 2B:
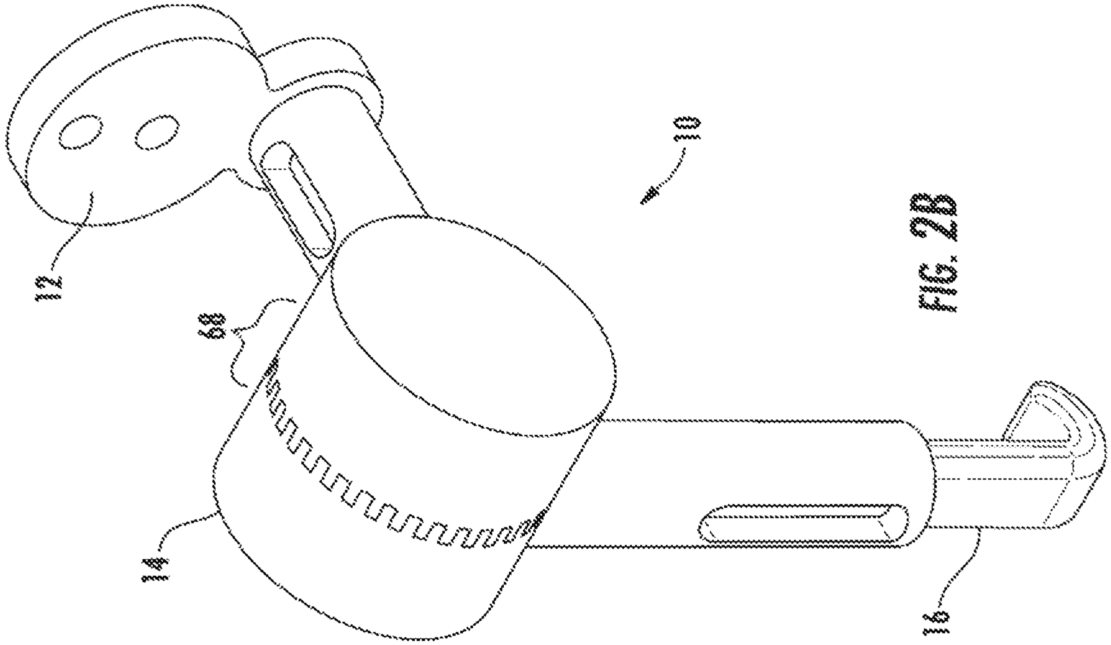
FIG. 2B is an alternative perspective view of the nerve retractor with a non-angled post and main body orientation.
Figure 2A:
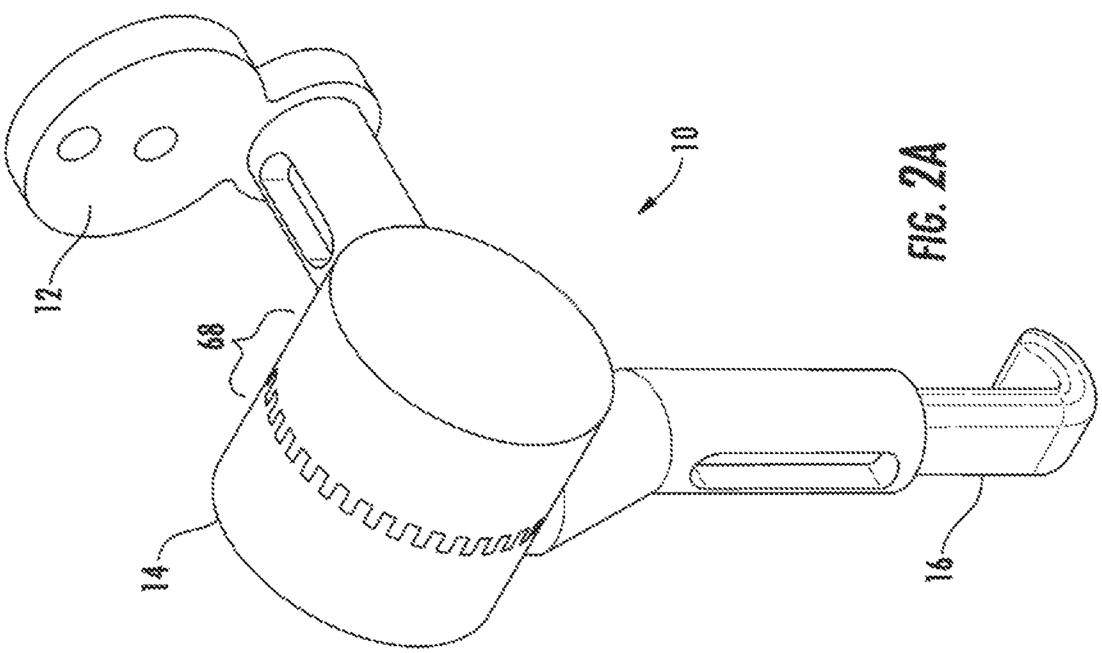
FIG. 2A is an alternative perspective view of the nerve retractor which allows the user to change the orientation and angle of the nerve retractor.

Referring to FIGS. 1A and 2A, an illustrative embodiment of a nerve retractor, preferably a nerve root retractor, referred to generally as nerve retractor 10, is shown. The nerve retractor 10 is designed to allow a user, such as a surgeon or assistant, to steadily retract a spinal sac and nerve root that travel through the spinal canal. The nerve retractor 10 provides easier and safer access to the surgical target and allows the surgeon to work without damaging vital neural structures. Under current surgical protocols, an independent member of the surgical team, such as a surgical first assistant, retracts the nerve root and spinal sac and holds them in place while the surgeon operates. The nerve retractor 10 is designed to attach to a portion of the spine, allowing it to move with a changing patient orientation or movement, and eliminates the requirement of having the independent member hold the retractor tool, thus providing a safer procedure. While the nerve retractor 10 may be described in the context of spinal surgery, such surgical use is illustrative only. Other surgical procedures, such as spinal procedures or other procedures that may encounter or require retraction of nerves, may find use with the nerve retractor 10. Preferably, the nerve retractor 10 comprises three components, a base portion 12, an arm portion 14, and an anatomical structure retractor portion 16.

The nerve retractor 10 may be constructed from any material known to one of skill that can be used for a surgical tool and for surgical procedures. For example, one or more parts of the nerve retractor may be made of a polycarbonate material. One or more components may be made from any process known to one of skill in the art, including injection molding or 3D printing. The nerve retractor 10 may be made as a single unit or in multiple components and secured together to form the single unit.

Referring to FIGS. 3-8, an illustrative example of the base portion 12 is shown in greater detail. The base portion 12 is configured to have at least one portion engage with or secure to at least a portion of an anatomical structure of an animal, such as a human, and at least one portion that interacts with the arm 14. The base portion 12 comprises an anatomical structure engaging member, illustrated herein as a base plate 18, a first member of a retractor actuating member 20, (also referred to as first retractor actuating member 20), and an interconnecting member 22. The base plate 18 is configured to engage with or be secured to at least a portion of an anatomical structure, such as at least a portion of the spine, more preferably the spinous process. The base plate 18 shown in FIGS. 3-8 comprises an inner surface 24 and an outer surface 26.

When used as part of a surgical procedure, i.e. the base plate 18 is secured to an anatomical structure, the outer surface 26 is in direct contact with the surface of the anatomical structure. The base plate is made of an upper portion 28 and a lower portion 30. The upper portion has a larger diameter 32 through the center than the diameter 34 through the center of the lower portion 30. While the upper portion 28 and the lower portion 30 each assume a circular or generally circular shape, together forming a figure "8" like shape, such shape is illustrative only. As such, the base plate 18 may have any shape overall, and the upper portion 28 and the lower portion 30 may have different shapes, independently, i.e., one square and one hexagonal, or the same, i.e. both having a hexagonal shape.

The upper portion 28 may comprise one or more openings 36 sized and shaped to receive a securing device, such as a screw. Each opening 36 may include threading (male or female) 38 to accommodate and secure with the threading (female or male) associated with a threaded screw.

Figure 6A:
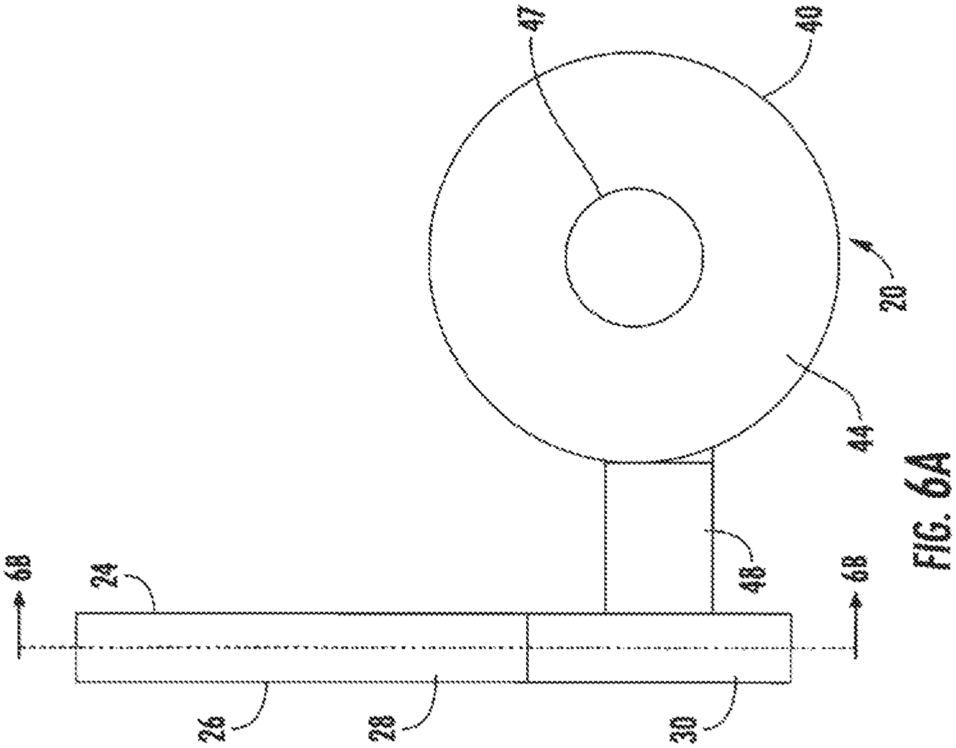
FIG. 6A is a right side view of the base portion of the nerve retractor.
Figure 5:
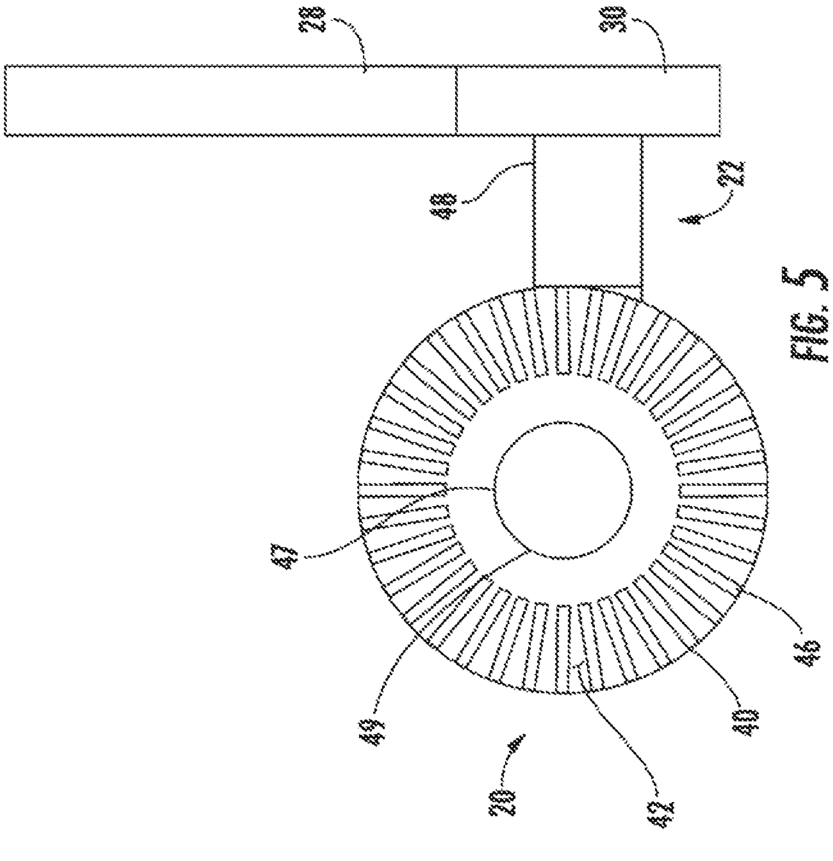
FIG. 5 is a left side view of the base portion of the nerve retractor.

The first retractor actuating member 20 is configured to interact with a second retractor actuating member, together forming the retractor actuating unit (to be described later). The first retractor actuating member 20 is illustrated as a circular or wheel shaped body 40 having an inner surface 42 (FIG. 5) and an outer surface 44 (FIG. 6A). The outer surface 44 preferably has a generally planar and smooth surface. The inner surface 42 has a plurality of teeth 46 (may also be referred to as first teeth 46 or first retractor actuating member teeth 46), circumferentially arranged and spaced apart. Each of the plurality of teeth 46 are sized, shaped and arranged to engage or interconnect with a second set of teeth (to be described later) associated with the second retractor actuating member. The first retractor actuating member 20 may contain an opening 47, preferably with threading 49, to engage and secure with a portion of the arm 14.

The base plate 18 and the first retractor actuating member 20 are linked together through the interconnecting member 22. The interconnecting member 22 is illustrated herein as a generally tubular body 48 (see FIG. 5) which provides separation length between the base plate 18 and the first retractor actuating member 20. The interconnecting member 22 may be integrally formed from the base plate 18, the first retractor actuating member 20, or both the base plate 18 and the first retractor actuating member 20.

The interconnecting member 22 may be configured to allow the first retractor actuating member 20 to change positions, i.e. moving closer to or further away from the base plate 18. In one illustrative example, the interconnecting member tubular body 48 may be hollow, or partially hollow, having an interior lumen 50 (see FIG. 6B) sized and shaped to receive a portion of the first retractor actuating member 20. As illustrated, the first retractor actuating member 20 includes a stem portion 52 sized and shaped to extend into the interconnecting member tubular body lumen 50. To traverse from one position, i.e. closer to the base plate 18, to a second position, i.e. further from the base plate 18, a user could simply move the interconnecting member 22 in a linear direction away from the base plate 18 (or in a reverse direction, towards the base plate 18) to a desired location, see FIG. 6C, moved away from the base plate 18 when compared to FIG. 6B. Once placed in the desired location, the interconnecting member 22 may be locked in place.

Figure 3:
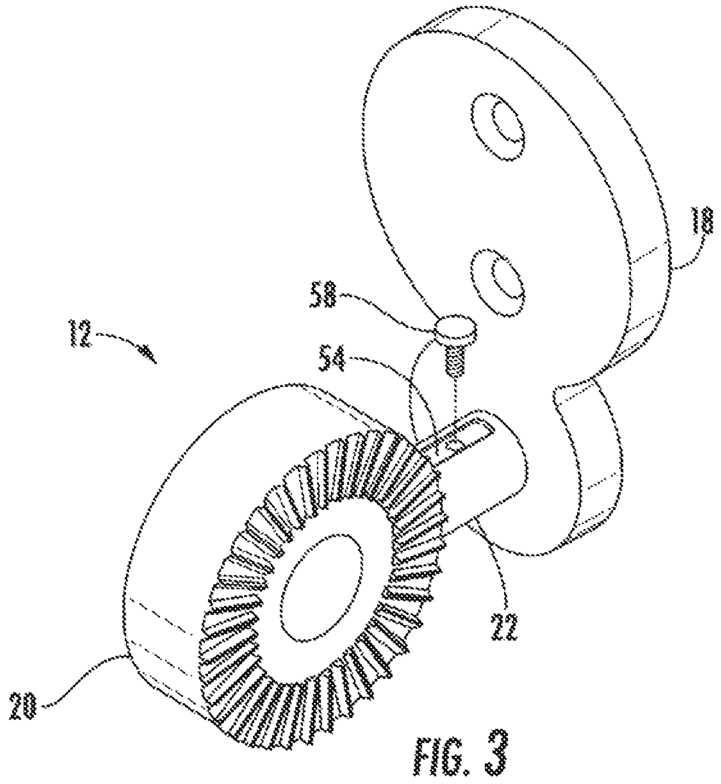
FIG. 3 is a perspective view of an illustrative embodiment of a base portion of the nerve retractor which allows the user to change the orientation and angle of the nerve retractor.
Figure 4:
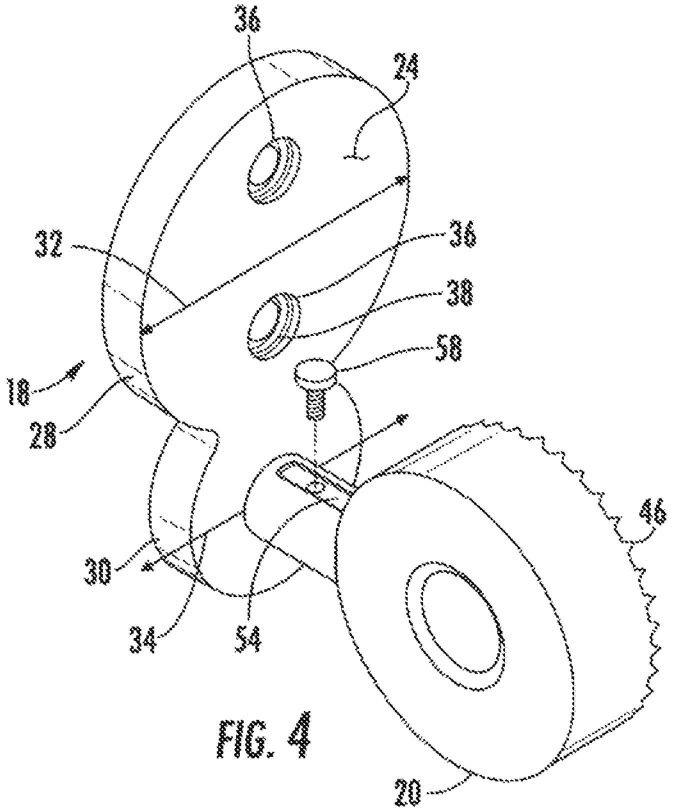
FIG. 4 is an alternative perspective view of the base portion of the nerve retractor which allows the user to change the orientation and angle of the nerve retractor.
Figure 6C:
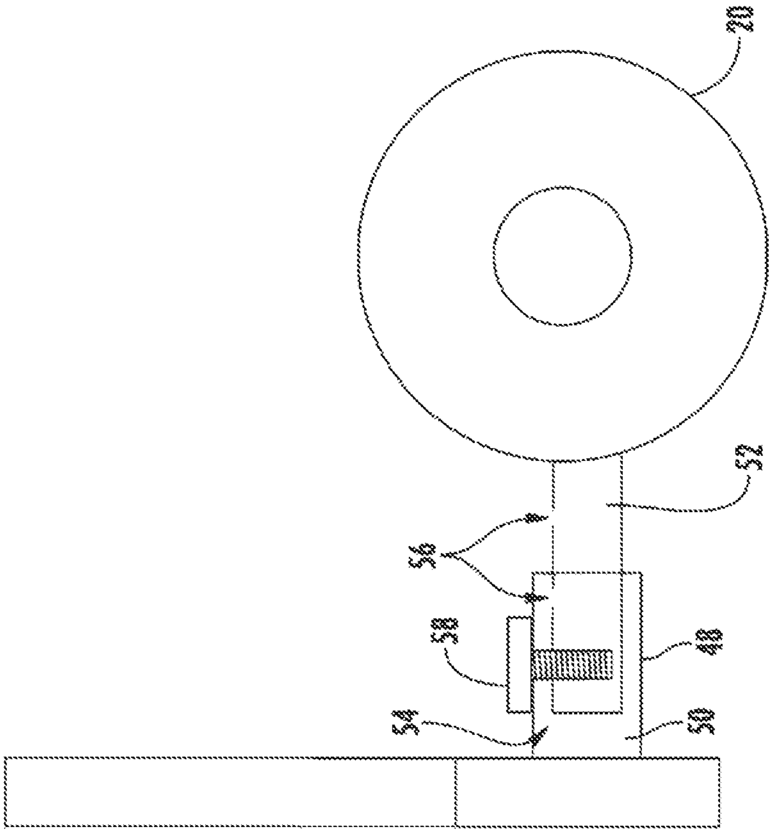
FIG. 6C is a cross sectional view taken along lines 6B-6B of FIG. 6A, illustrating the first retractor actuating member in a second position, further from the base portion when compared to FIG. 6B.
Figure 6B:
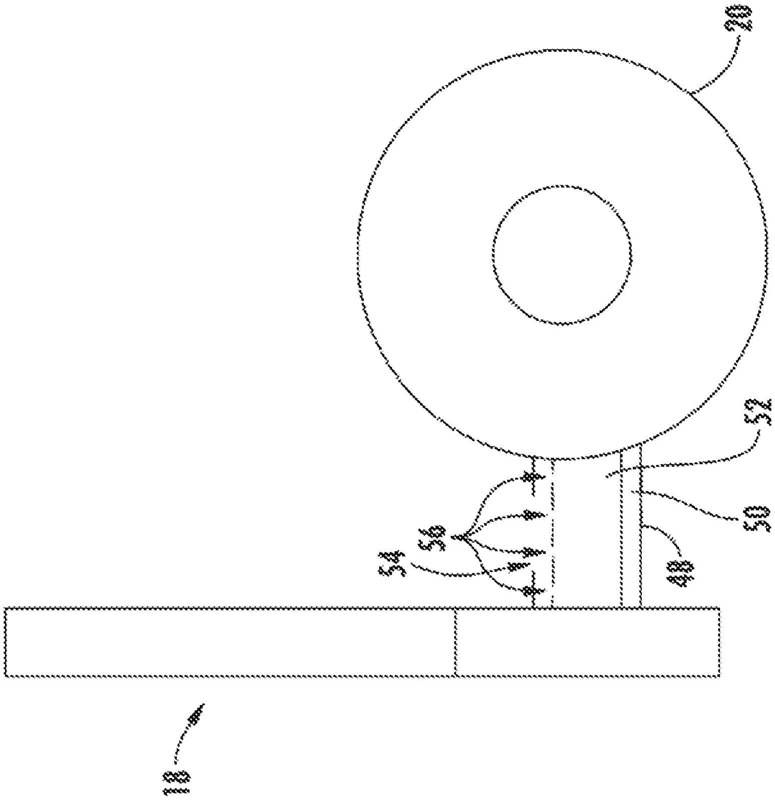
FIG. 6B is a cross sectional view taken along lines 6B-6B of FIG. 6A, illustrating a first retractor actuating member in a first position, close to a base portion.
Figure 7:
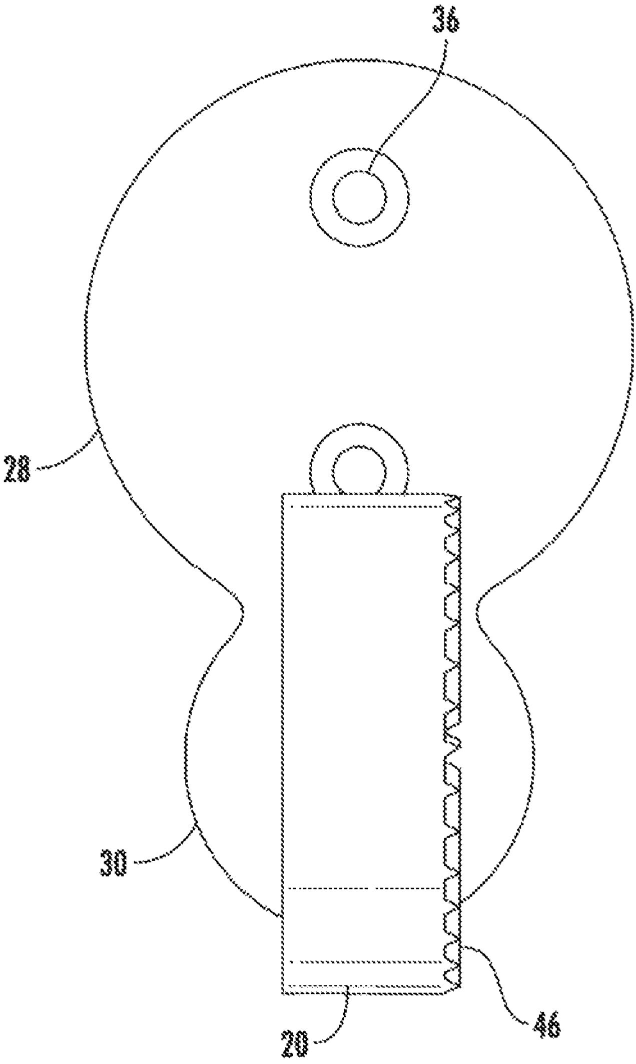
FIG. 7 is a front view of the base portion of the nerve retractor.
Figure 8:
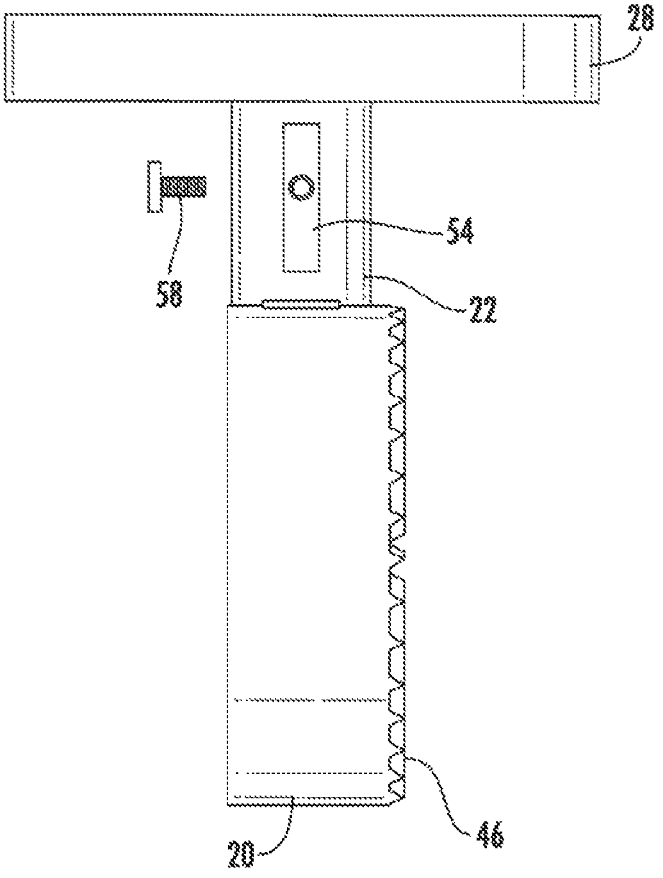
FIG. 8 is a top view of the base portion of the nerve retractor.
Figure 9:
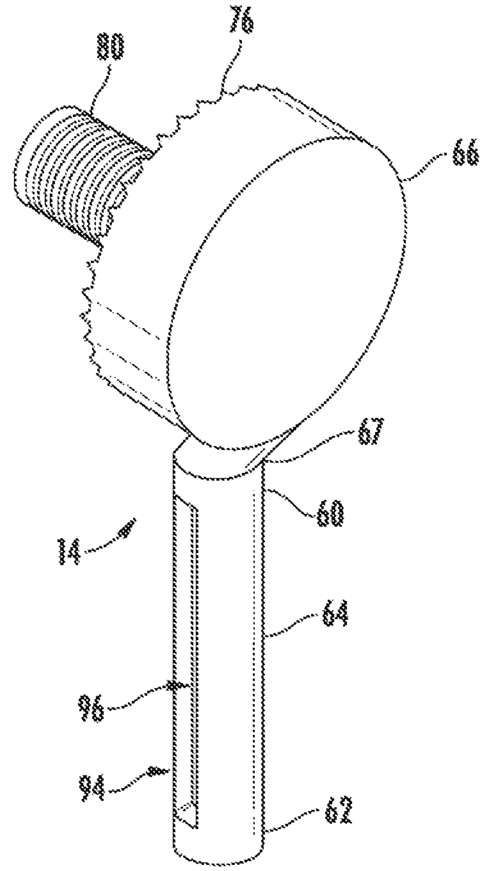
FIG. 9 is a back perspective view of an illustrative embodiment of an arm portion of the nerve retractor.
Figure 10:
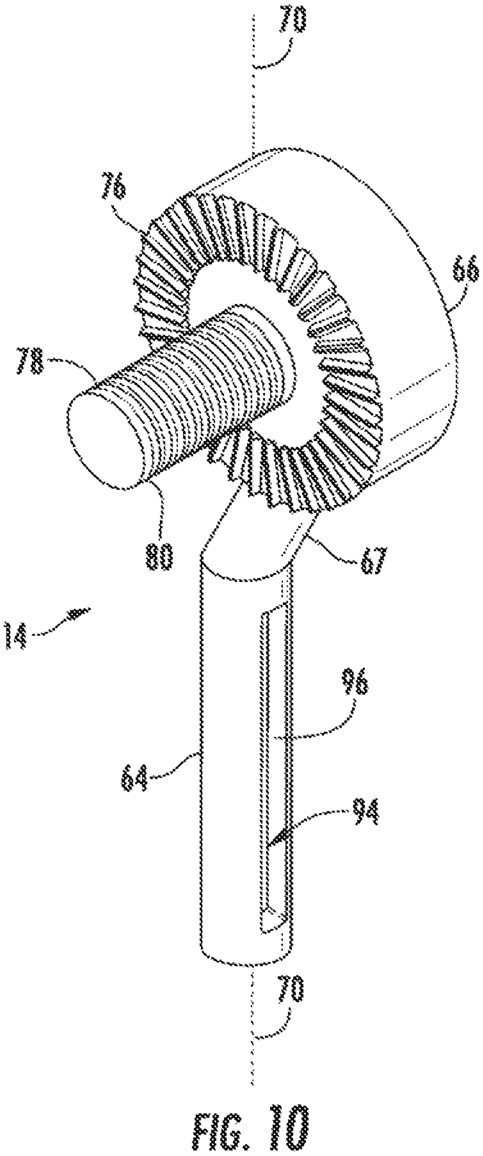
FIG. 10 is a front perspective view of the arm portion of the nerve retractor.
Figure 11:
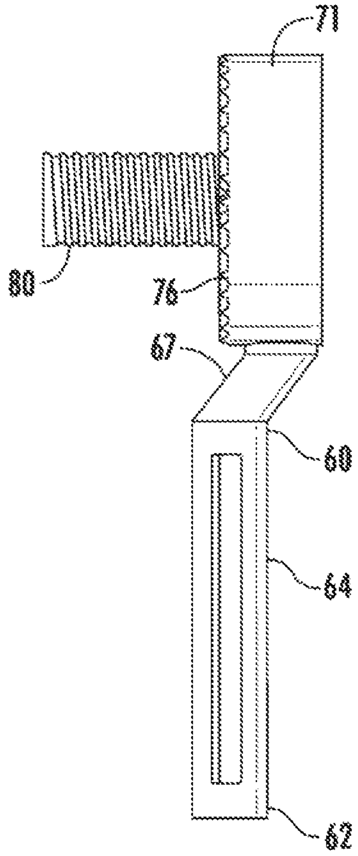
FIG. 11 is a side view of the arm portion of the nerve retractor.

As shown in FIG. 3, FIG. 6B and FIG. 6C, the interconnecting member 22 has an opening, shown as a slotted opening or channel 54. The first retractor actuating member stem portion 52 may contain one or more openings 56. Both interconnecting member slotted opening or channel 54 and the first retractor actuating member stem portion openings 56 are sized and shaped to receive and hold a fastening member, illustrated herein as a screw 58, such as a thumb screw, see FIG. 6C. Other fastening members, such as a pin, known to one of skill in the art may be used. Once the screw 58 is secured in place, the first retractor actuating member stem portion 52 is prevented from moving until the fastening member 58 is released, thus locking the first retractor actuating member 20 at a fixed distance from the base plate 18.

Alternatively, the interconnecting member 22 may be secured to, or formed from, the base plate 18 as a fixed unit. In this arrangement, the first retractor actuating member 20 is positioned off or away from the base plate 18 at a fixed, non-extendable/retractable distance.

Figure 21:
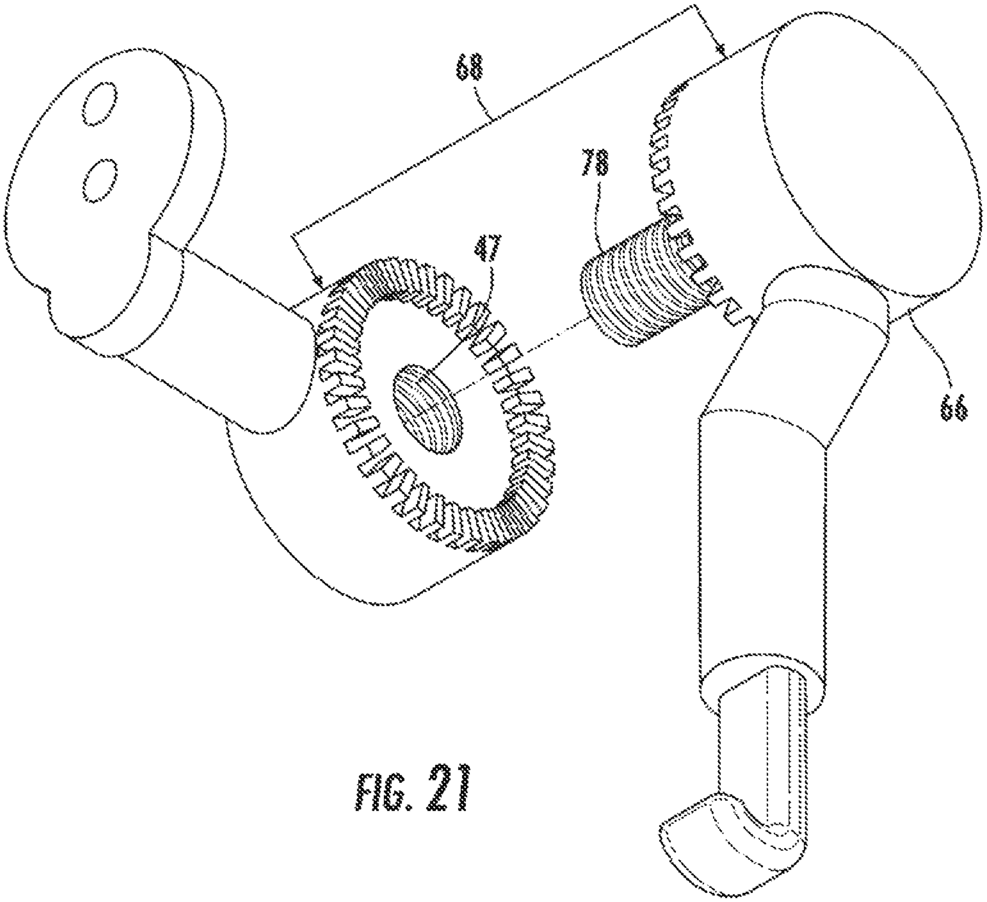
FIG. 21 is an exploded view of the nerve retractor.

FIGS. 9-13 illustrate an embodiment of the arm portion 14. The arm portion 14 comprises a first end 60, a second opposing end 62, and a main body 64 therebetween. Attached to or integrally formed to the first end 60 is a second member of a retractor actuating member 66 (also referred to as a second retractor actuating member 66). The second retractor actuating member 66 is configured to interact with the first retractor actuating member 20. When secured or interacting together, the first retractor actuating member 20 and the second retractor actuating member 66 form the retractor actuating unit, referred to generally, i.e. both components together, as retractor actuator 68, see FIG. 1A, FIG. 1B or FIG. 21. The retractor actuator 68 is designed and functions to move and set the arm portion 14 at various angles. Moving and setting the arm portion 14 at various angles allows the anatomical structure retractor portion 16 to be moved and set at different angles as well, allowing the surgeon to retract a nerve root as far back as needed. The second retractor actuating member 66 extends or connects from the first end 60 via a post 67. The post 67 is shown angled from the main body 64; positioning the second retractor actuating member 66 off center from a longitudinal axis 70, see FIG. 10. Alternatively, the second retractor actuating member 66 extends or connects from the first end 60 with or without a post 67, so the second retractor actuating member 66 is positioned on center with the longitudinal axis 70 (i.e. linear, not forming an angled connection), see FIG. 1B or FIG. 2B.

Figure 12:
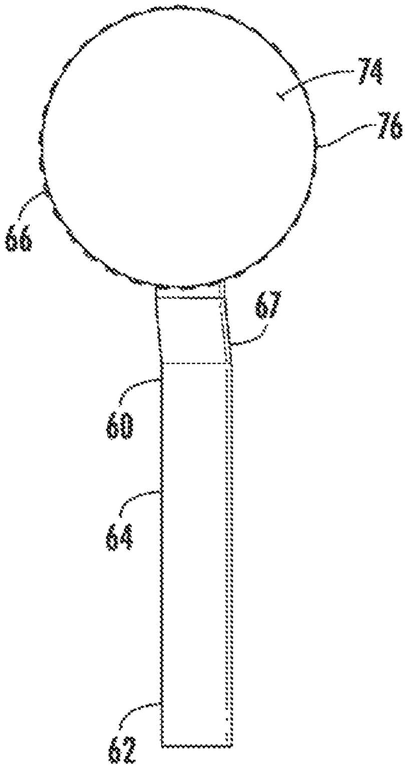
FIG. 12 is a back elevation view of the arm portion of the nerve retractor.
Figure 13:
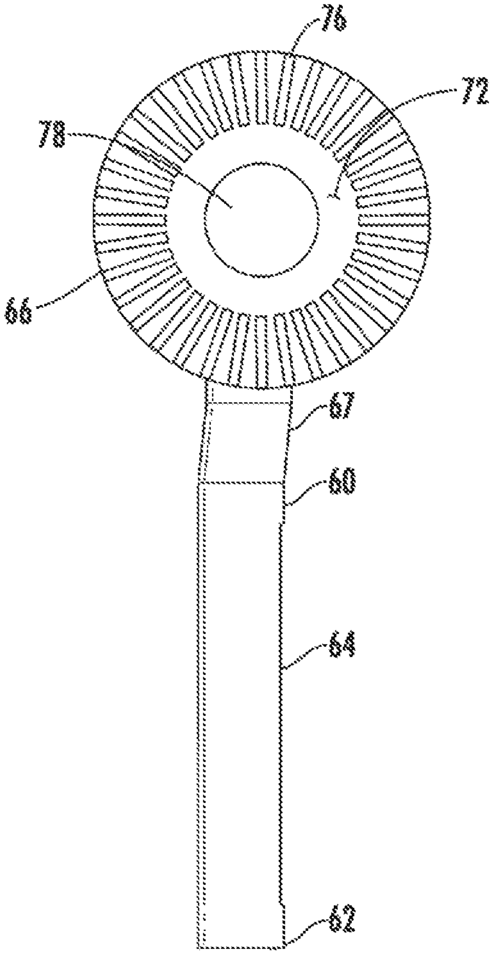
FIG. 13 is a front elevation view of the arm portion of the nerve retractor.

The second retractor actuating member 66 is illustrated as a circular or wheel shaped body 71 having an inner surface 72 (FIG. 13) and an outer surface 74 (FIG. 12). The outer surface 74 preferably has a generally planar and smooth surface. The inner surface 72 has a plurality of teeth 76 (may also be referred to as second teeth 76 or second retractor actuating member teeth 76), circumferentially arranged and spaced apart. Each of the plurality of teeth 76 are sized, shaped and arranged to engage or interconnect with the first set of teeth 46 associated with the first retractor actuating member 20.

Figure 22:
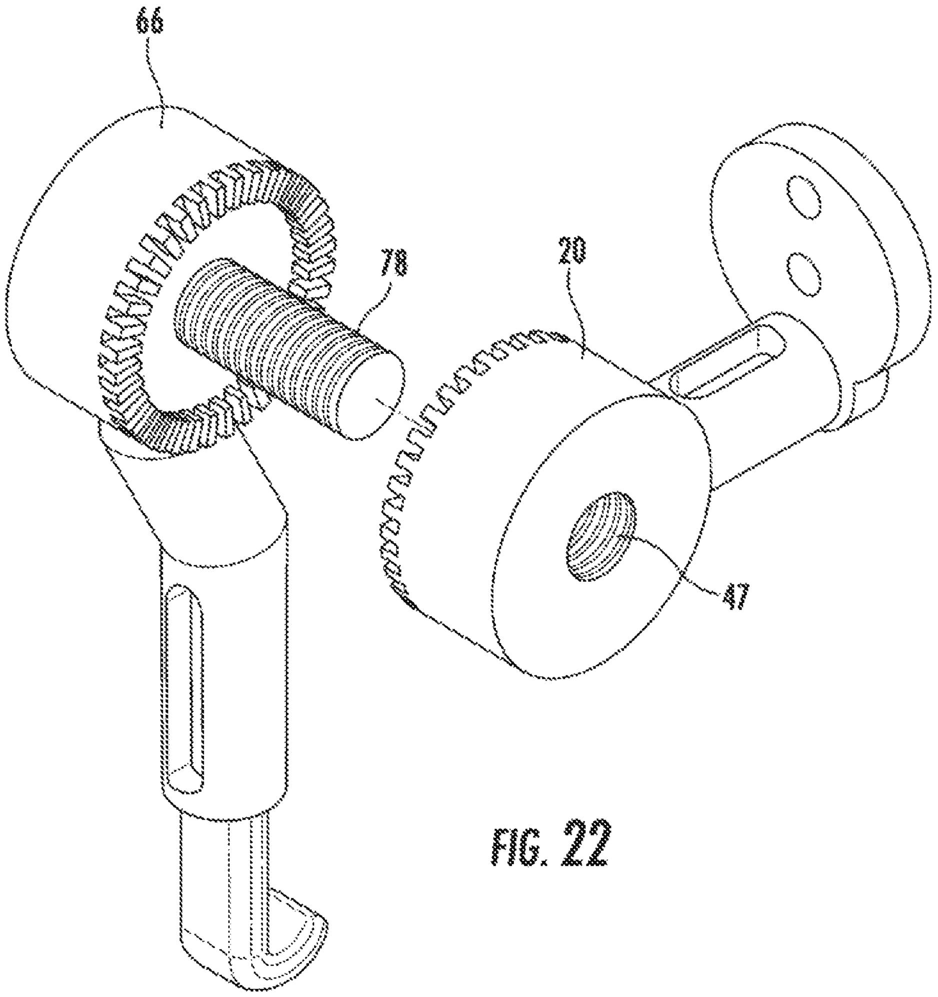
FIG. 22 is an alternative view of the nerve retractor.

Extending from the second retractor actuating member inner surface 72, preferably from the center thereof, is a first retractor actuating engagement member 78 configured to engage with or secure to the first retractor actuating member 20, thus locking (preventing the angled movement of the arm 14) or unlocking (allowing angled movement of the arm 14) the retractor actuator 68. The first retractor actuating engagement member 78 is illustrated as a threaded rod 80, and is configured to engage or interact with threading 49 associated the first retractor actuating member opening 47, see FIGS. 21 and 22.

Attached to, or integrally formed from, the second retractor actuating member 66 is the anatomical structure retractor 16. Preferably, the anatomical structure retractor 16 extends from and away from the second end 62 of the second retractor actuating member 66. FIGS. 14A-20 illustrate an embodiment of the anatomical structure retractor 16. The anatomical structure retractor 16 comprises a first end 82 (may also be referred to as a top end), an opposing second end 84 (may also be referred to as a bottom end), and a main body 86 therebetween. The main body 86 is further defined by a right side or surface 81 and a left side or surface 83. The anatomical structure retractor 16 also comprises a first upper or outer side or surface 85 and a second bottom or inner side or surface 87. The anatomical structure retractor main body 86 is shown having an elongated, generally rectangular shape which provides the anatomical structure retractor with a length. However, the anatomical structure retractor main body 86 may assume any shape necessary to function. The anatomical structure retractor first end 82 is configured to connect with or to a portion of the arm 14, preferably the arm main body 64. Alternatively, the anatomical structure retractor 16 may be integrally formed from the arm portion 14.

The anatomical structure retractor second end 84, which is located furthest away from the base portion 12, is configured to interact with the anatomical structure of the patient when in use. Accordingly, the anatomical structure retractor second end 84 comprises an anatomical structure engaging member 90, illustrated herein as a curved body 88, forming a J-shaped hooked end 87, FIG. 14A. The anatomical structure engaging member may be a separate unit and secured or connected to the anatomical structure retractor second end 84.

The anatomical structure engaging member 90 may be a modular unit, providing a modular nerve retractor 10 having a modular anatomical structure engaging member or head 90 which can be attached and secured or removed from the anatomical structure retractor second end 84. The modular anatomical structure engaging member or head 90 is preferably secured to the anatomical structure retractor second end 84 via a thumb screw 58, or other mechanisms, such as a snap or spring lock mechanism in which the modular anatomical structure engaging member or head 90 is made of a material that expands when inserted into the anatomical structure retractor second end 84 and snaps back after the insertion force is applied. Alternatively, the modular anatomical structure engaging member or head 90 may be constructed as a one-piece arm and hook. The modular anatomical structure engaging member or head 90 allows the user to easily and quickly change the head units based on individual surgical needs or procedures. Alternatively, the anatomical structure engaging member or head 90 may be integrally formed from the anatomical structure retractor 16.

Figure 14A:
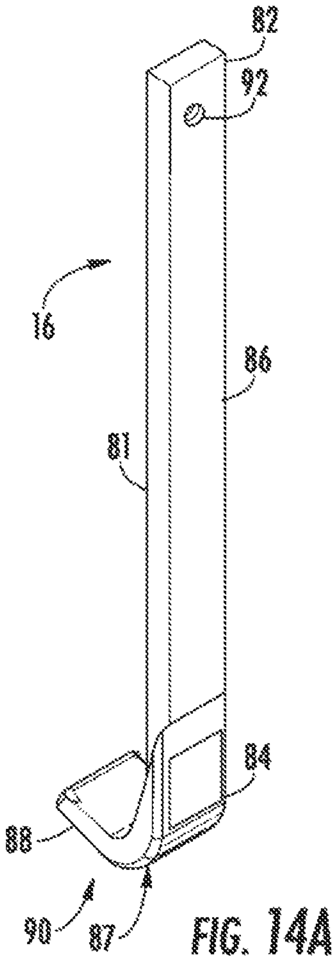
FIG. 14A is a right side, upper surface perspective view of an illustrative embodiment of a retractor portion of the nerve retractor, shown with a J-shaped modular head unit.
Figure 14B:
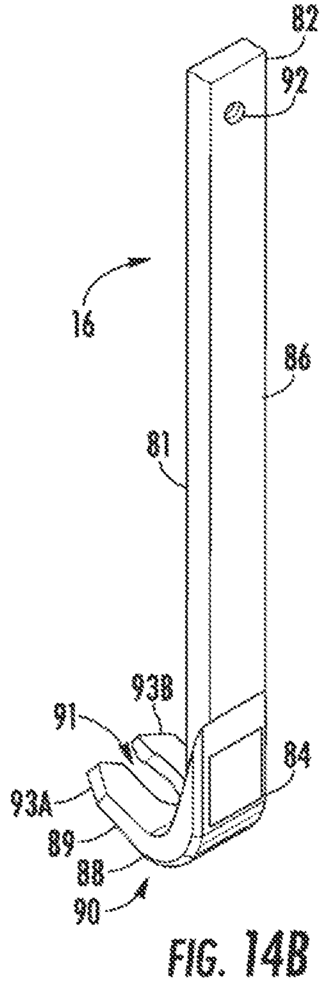
FIG. 14B is a perspective view of the retractor portion of the nerve retractor illustrated in FIG. 14A, shown with a forked shaped modular head unit.
Figure 14C:
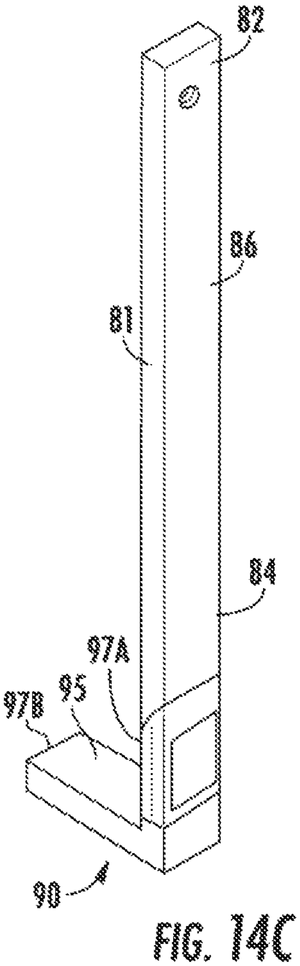
FIG. 14C is a perspective view of the retractor portion of the nerve retractor illustrated in FIG. 14A, shown with an L-shaped modular head unit.
Figure 15:
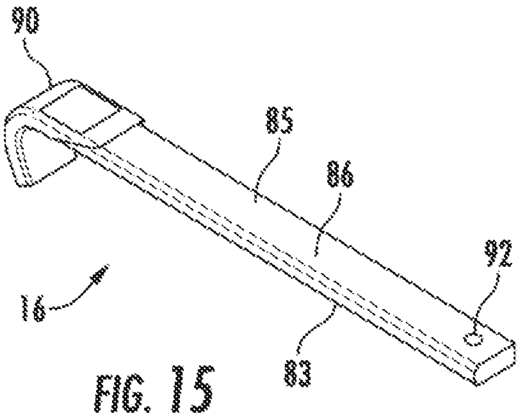
FIG. 15 is a left side, outer surface, top perspective view of the retractor portion of the nerve retractor.
Figure 16:
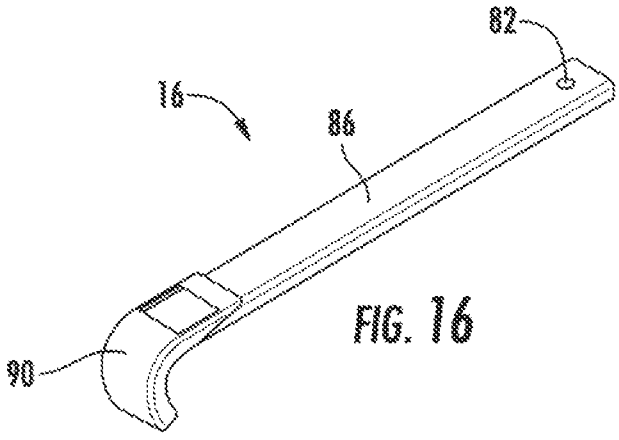
FIG. 16 is a left side, outer surface, bottom perspective view of the retractor portion of the nerve retractor.
Figure 17:
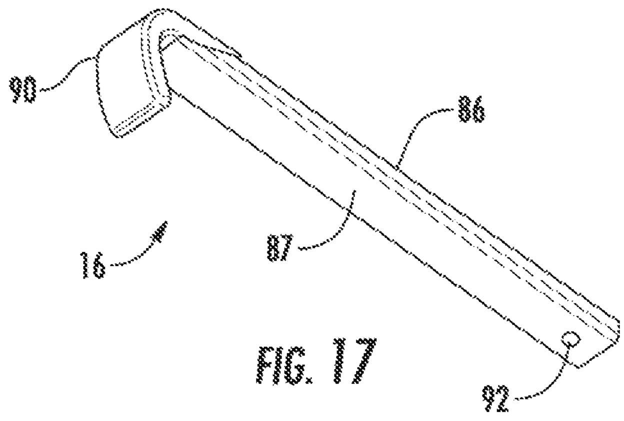
FIG. 17 is a left side, inner surface, top perspective view of the retractor portion of the nerve retractor.
Figure 18:
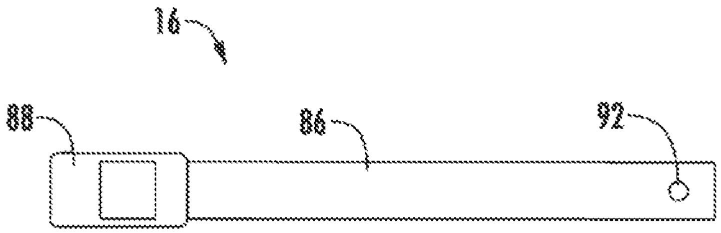
FIG. 18 is a top view of the retractor portion of the nerve retractor.
Figure 19:
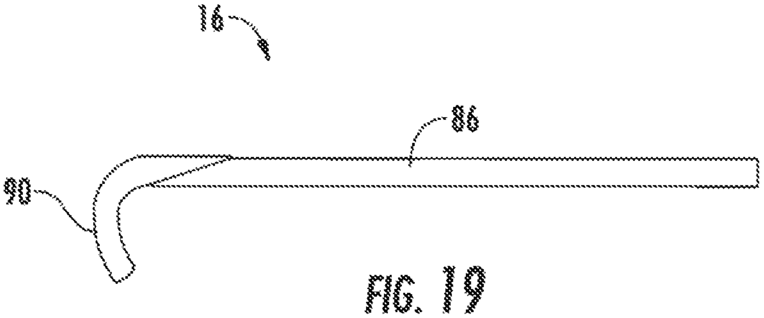
FIG. 19 is a left side view of the retractor portion of the nerve retractor.
Figure 20:
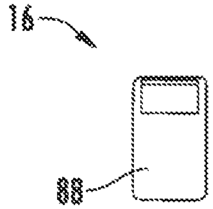
FIG. 20 is a front view of the retractor portion of the nerve retractor.

The J-shaped hooked end 87 allows the user to safely, i.e. not damage the structure, engage or interact with the anatomical structure, moving it from its original location, and out of the field where the user may need to operate or perform a procedure. FIG. 14B illustrates an anatomical structure engaging member or head 90 or a modular anatomical structure engaging member or head 90, shown as a fork-like structure 89, in which the curved surface 88 contains a gap 91 separating independent prongs or finger-like extensions 93A and 93B. FIG. 14C illustrates an anatomical structure engaging member or head 90 or a modular anatomical structure engaging member or head 90, having an L-shaped structure 95. The L-shaped structure 95 includes a first surface 97A and a second surface 97B. The second surface 97B is arranged in a generally perpendicular orientation relative to the first surface 97A. FIG. 14D illustrates an anatomical structure engaging member or head 90 or a modular anatomical structure engaging member or head 90, shown as a curved blade 61. FIG. 14E illustrates an anatomical structure engaging member or head 90 or a modular anatomical structure engaging member or head 90, shown having an alternative curved blade 63. FIG. 14F illustrates an anatomical structure engaging member or head 90 or a modular anatomical structure engaging member or head 90, shown having a bayonet blade 65. FIG. 14G illustrates an anatomical structure engaging member or head 90 or a modular anatomical structure engaging member or head 90, shown having a paddle blade 67. FIG. 14H illustrates an anatomical structure engaging member or head 90 or a modular anatomical structure engaging member or head 90, shown having a generally flat surface with a curved tip blade 69.

The nerve retractor 10 may be configured so the retractor portion 16 is adjustable. Accordingly, the arm portion main body 64 is configured to receive at least a portion of the anatomical structure retractor main body 86. The anatomical structure retractor first end 82 is shown having a threaded opening 92. The threaded opening 92 is sized, shaped, and configured to receive a fastening member such as a screw 58. The arm portion main body 64 may contain an interior portion 94, see FIGS. 9 and 10, to receive and hold a portion of the anatomical structure retractor 16 therein. A slotted opening 96 allows the user to insert a fastening member, such as a screw, into the arm main body interior portion 94, inserting the screw into the anatomical structure retractor first end 82 threaded opening 92. Where the anatomical structure retractor 16 is inserted into the arm portion main body 64 and secured in place defines the positioning and the length of the anatomical structure retractor 16.

Figure 23:
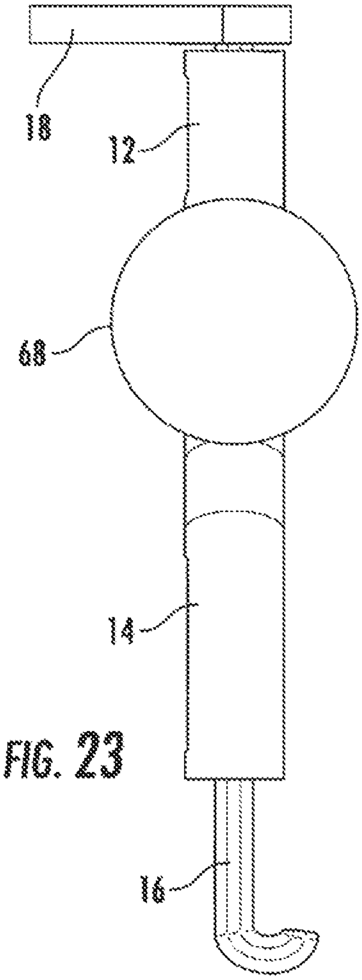
FIG. 23 illustrates the nerve retractor in a non-angled orientation.
Figure 24:
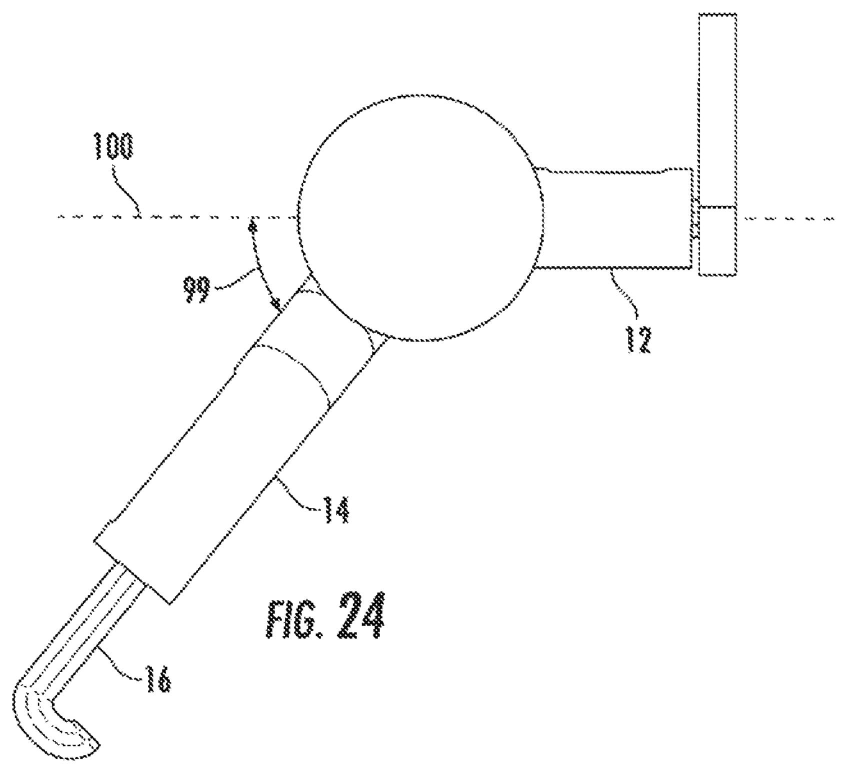
FIG. 24 illustrates the nerve retractor in an angled orientation, shown with the retractor rotated about 45 degrees.
Figure 25:
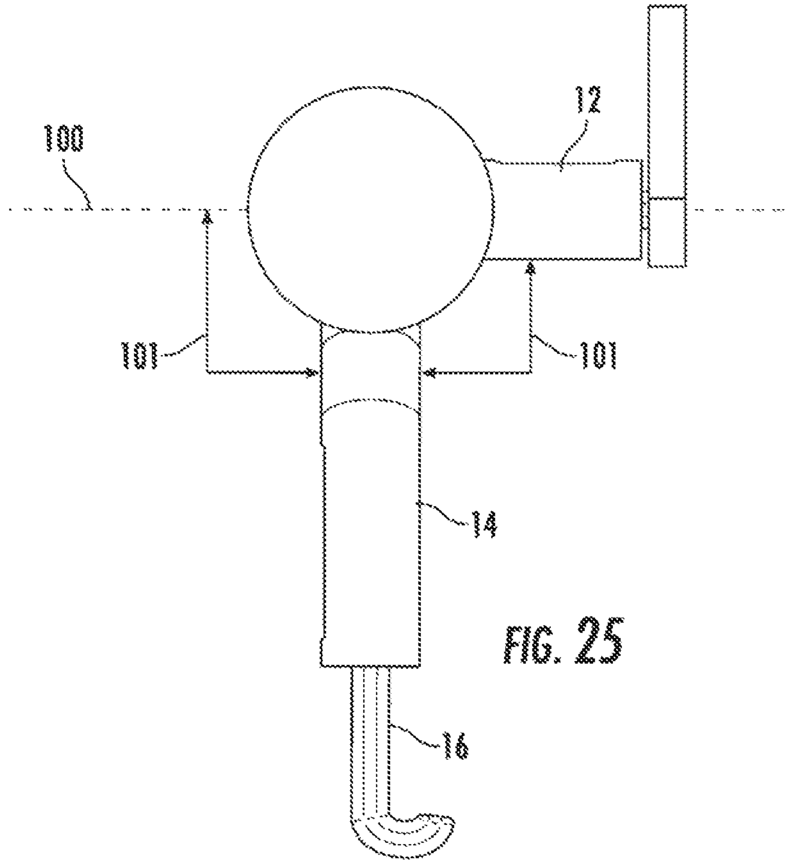
FIG. 25 illustrates the nerve retractor in an angled orientation, shown with the retractor rotated about 90 degrees.

FIGS. 23-25 illustrate the nerve retractor 10 in various orientations, defined by the location and position of the arm portion 14 or the retractor portion 16. As illustrated, the retractor actuator 68 is intact so that the user can move the arm portion 14 or the retractor portion 16. In this configuration, the first retractor actuating member 20 is engaged with the second retractor actuating member 66 so that the first retractor actuating member teeth 46 interact with the second retractor actuating member teeth 76. Since the base portion 12 is secured to an anatomical structure when in use, the second retractor actuating member 66 is moved, in this case rotated relative to the first retractor actuating member 20. As the surgeon rotates the second retractor actuating member 66 (or the arm main body 64 or retractor main body 86), the second retractor actuating member teeth 76 rotate, engaging with or securing to the first retractor actuating member teeth 46 above or below (depending on the direction and number of rotation(s)).

Based on the direction and number of rotation(s), the arm portion 14, and thus the retractor portion 16, may be positioned in any number of angled positions. FIG. 23 illustrates the nerve retractor in a traversed or non-manipulated orientation. In this arrangement, the arm portion 14 and the retractor portion 16 are in a linear position, with the hook end 90 being about 180 degrees apart from the base plate 18. FIG. 24 illustrates the nerve retractor 10 manipulated or traversed from the first position shown in FIG. 23 to a second position. In the second position, the arm portion 14 and the retractor portion 16 are arranged in a 45 degree angle (see 99, FIG. 24, relative to a longitudinal axis 100 and as moved from the orientation shown in FIG. 23).

FIG. 25 illustrates the nerve retractor 10 manipulated or traversed from the first position (FIG. 23) or the second position (shown in FIG. 24) to a third position. In the third position, the arm portion 14 and the retractor portion 16 are arranged in a 90 degree angle (see 101, FIG. 25, relative to a longitudinal axis 100 and as moved from the orientation shown in FIG. 23). While the nerve retractor 10 is illustrated with the arm portion 14 and the retractor portion 16 in various positions, no angle, 45 degree angle or 90 degree angle, the arm portion 14 and the anatomical structure retractor portion 16 may be traversed and set at any angle greater than 0 and less than 360 degrees. The nerve retractor 10 is preferably designed so that the arm portion 14 or the retractor portion 16 may be moved and/or locked at incremental positions or angles, such as between 0 and 360 degrees, between 0-45 degrees, between greater than zero degrees and 10 degrees, between 1 degree and 5 degrees, or at 1 degree increments. As a result of the construction of and interconnection between the first retractor actuating member 20 and the second retractor actuating member 66 the arm portion 14 and the retractor portion 16 may rotate in a sequential or step by step manner or distance.

Figure 28:
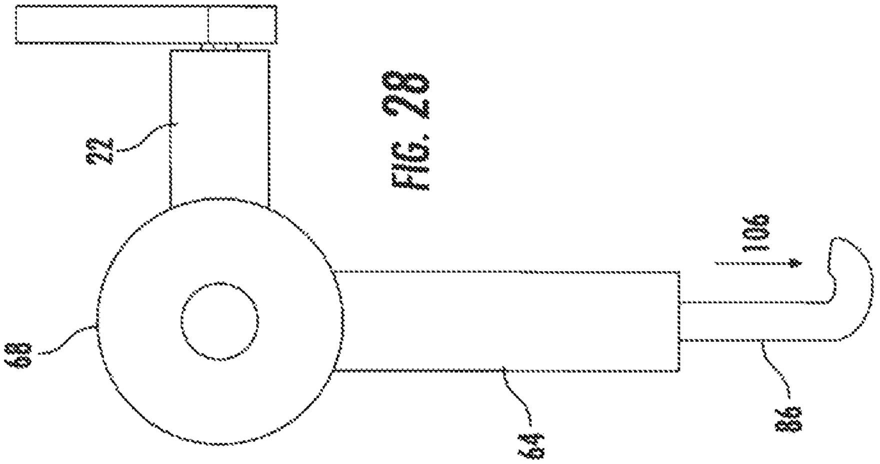
FIG. 28 illustrates the nerve retractor shown in FIG. 27, with the retractor back in its original position.
Figure 27:
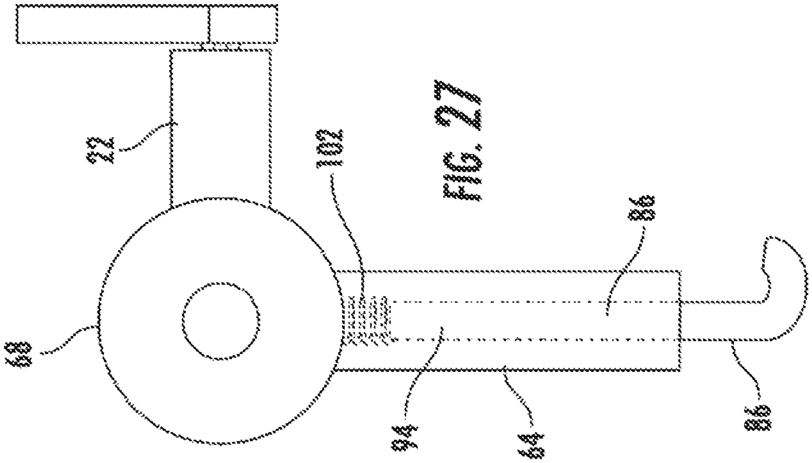
FIG. 27 illustrates the nerve retractor shown in FIG. 26, with the retractor in a retracted position.
Figure 26:
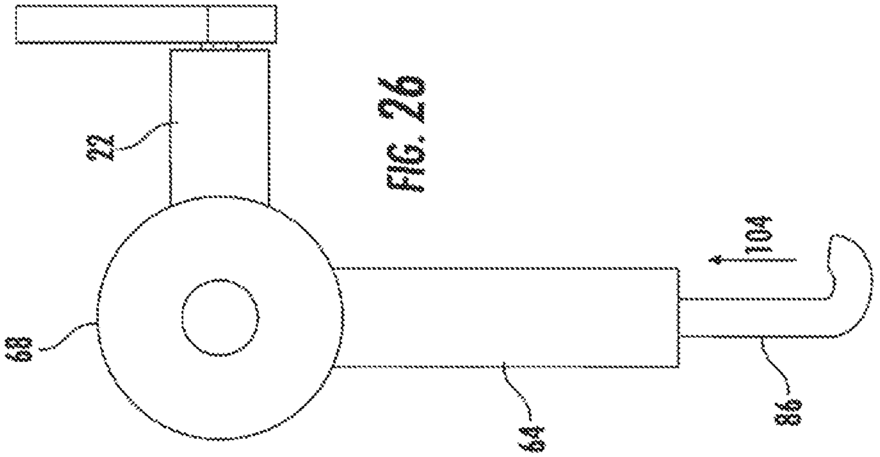
FIG. 26 illustrates an alternative embodiment of the nerve retractor.

FIGS. 26-28 illustrate an embodiment of the anatomical structure retractor portion 16 which may be spring loaded. The nerve retractor 10 may contain all the same components as described above, differing in how the anatomical structure retractor portion 16 moves in a linear manner into and out of a portion of the arm portion 14. A spring 102 placed within the arm main body interior portion 94 keeps the retractor portion 16 in place when no force is applied, see FIG. 27. Once a force is applied, such as from contact with an anatomical structure, the anatomical structure retractor 16 moves so that the anatomical structure retractor main body 86 moves inwardly, see arrow 104, FIG. 26, into the arm main body interior portion 94. Once the force is removed, the anatomical structure retractor portion 16 moves back to its original position, see arrow 106, FIG. 28.

Figure 29:
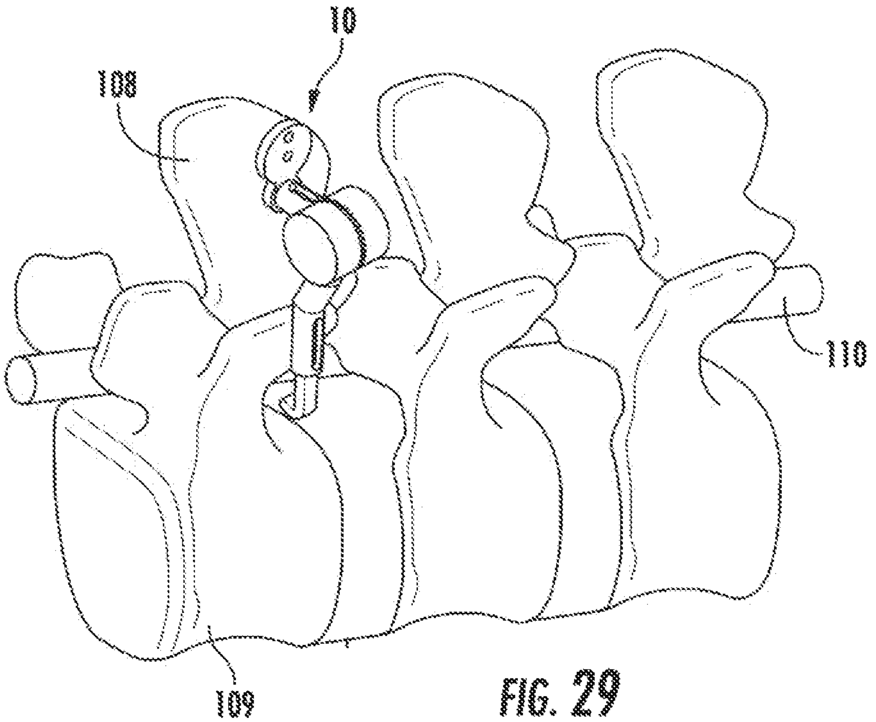
FIG. 29 illustrates the nerve retractor secured to a portion of the spine.
Figure 30:
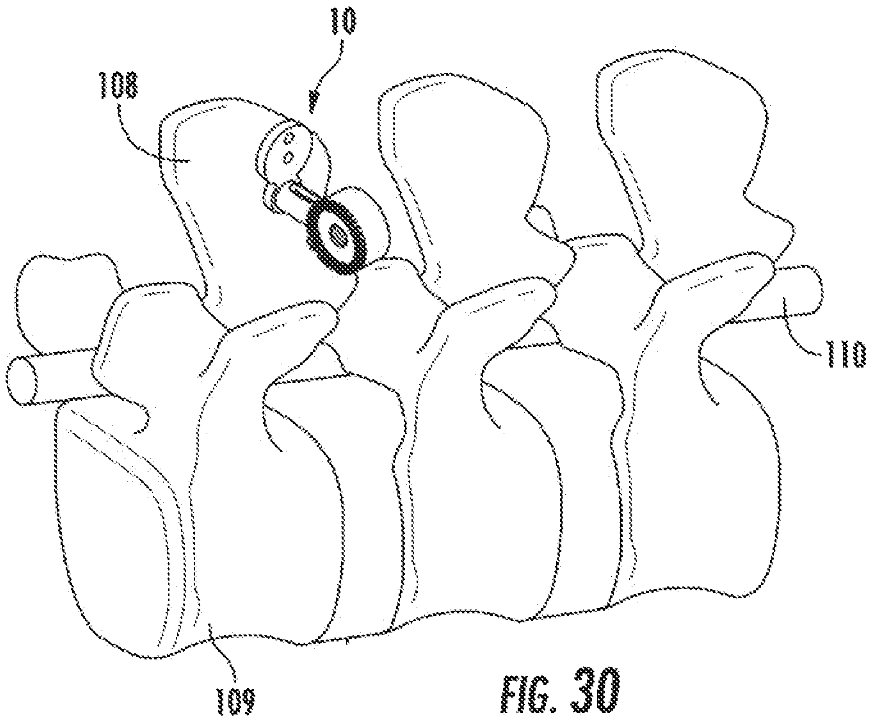
FIG. 30 illustrates the base portion of the nerve retractor secured to a portion of the spine.
Figure 31:
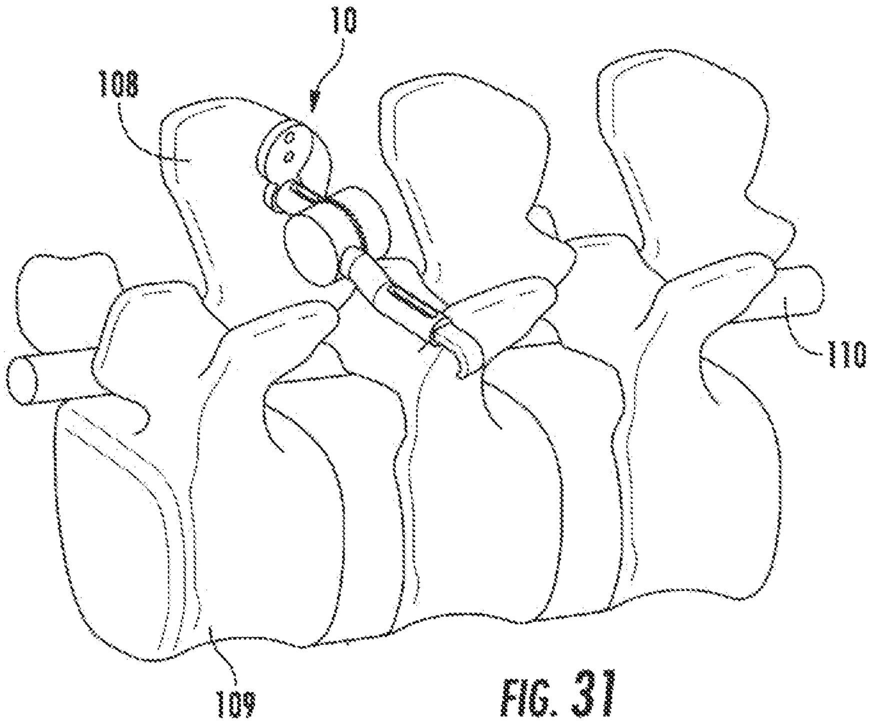
FIG. 31 illustrates the nerve retractor secured to a portion of the spine.
Figure 32:
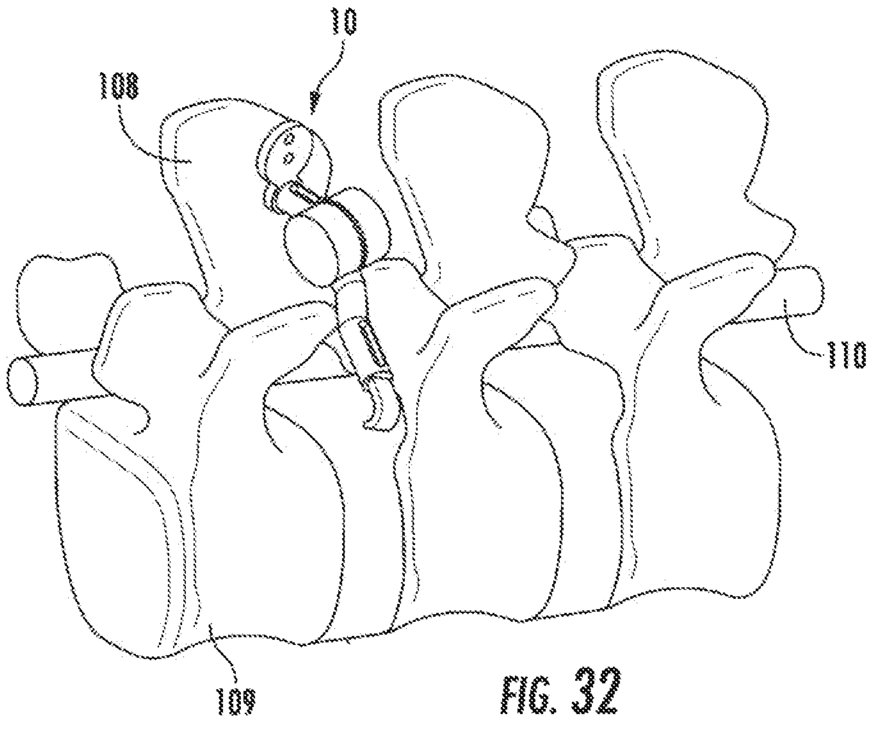
FIG. 32 illustrates the nerve retractor secured to a portion of the spine, with the retractor portion engaging with a nerve root.
Figure 33:
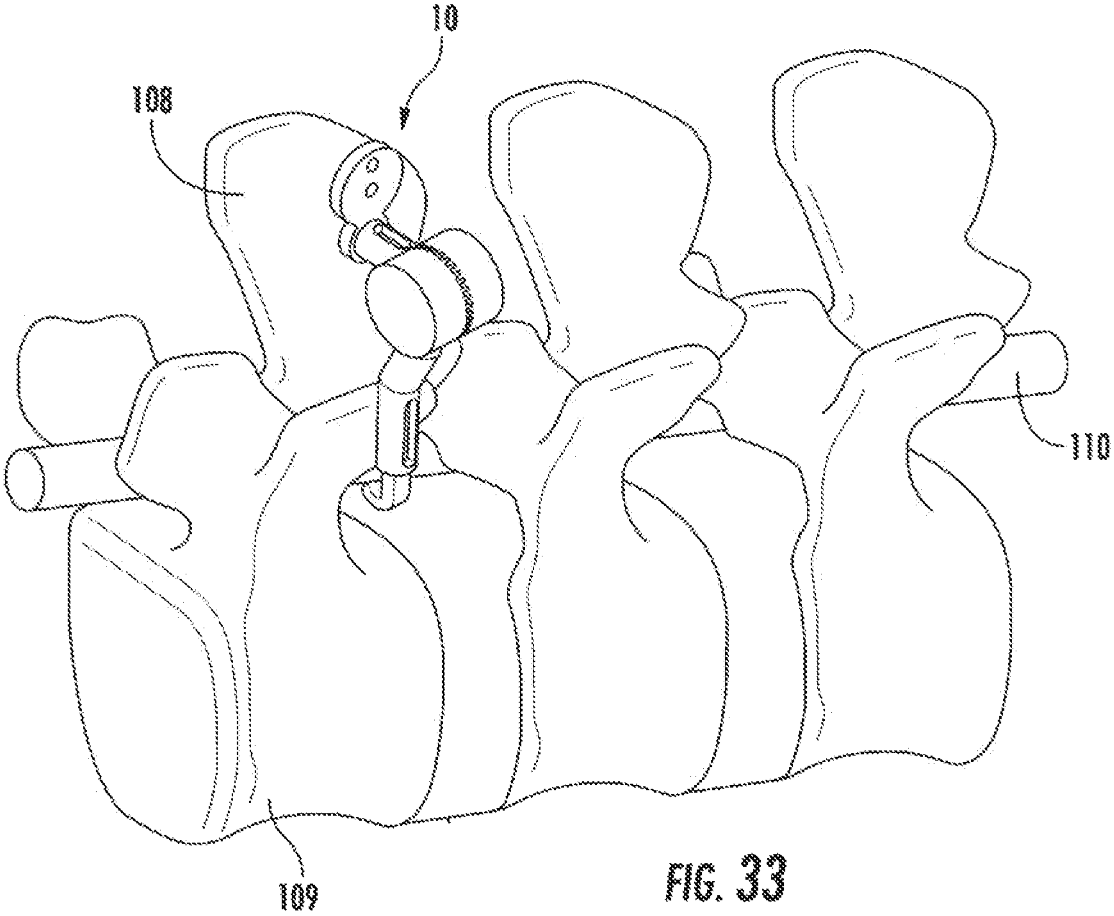
FIG. 33 illustrates the nerve retractor retracting the nerve root.

In use, the surgeon screws the base portion 12 into a patient's spine (spinous process) 108, see FIG. 29. Once the base portion 12 is in place, the surgeon then attaches the arm portion 14/anatomical structure retractor 16 and sets it in place via a hand screw, see FIG. 30. The arm portion 14/anatomical structure retractor 16 can be adjusted to the correct angle to engage the nerve root 110, see FIG. 31. FIG. 33 illustrates the nerve root 110 being retracted from the surgical area. If needed, the surgeon may loosen the hand screw to adjust the angle throughout the surgical procedure. In this manner, the surgeon can perform the operation without the need of an independent individual holding the retraction device.

Figure 34:
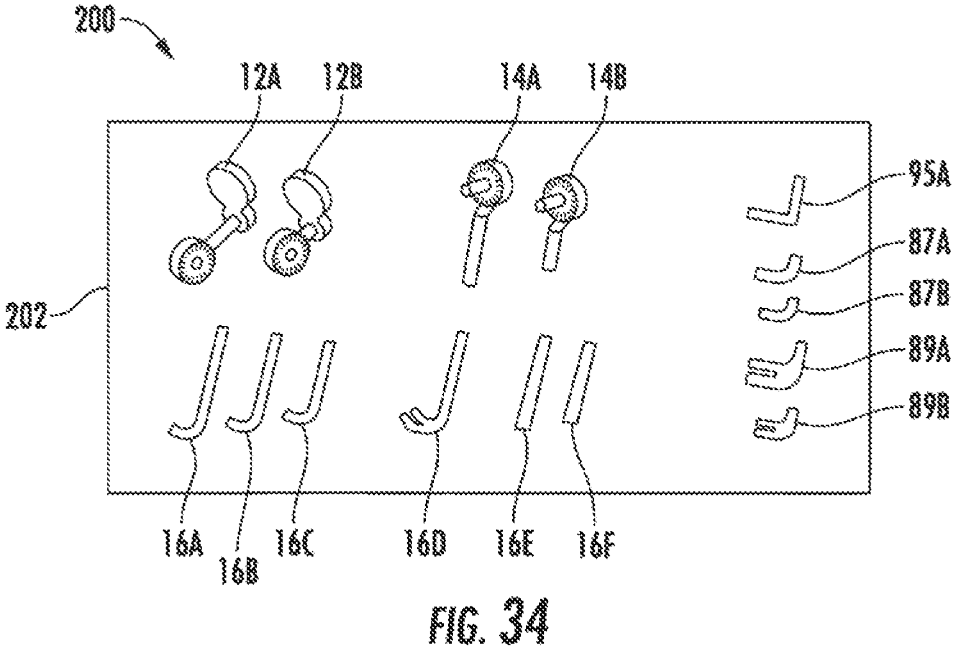
FIG. 34 illustrates a nerve retracting kit.

The nerve retractor 10 may be provided as a single unit, or as a kit including one or more of the components in any combination of components. FIG. 34 illustrates a nerve retractor kit 200 having an outer casing 202 holding one or more of, in any combination: 1) base portion 12, with same or multiple sizes, 12A being larger than 12B; 2) arm portion 14, with same or multiple sizes, 14A being larger than 14B; 3) anatomical structure retractor portion 16, including multiple and/or different sizes, large length body 16A, medium length body 16B, small length body 16C, fork shaped anatomical structure engaging member or head 16D, large (16E) and small (16F) bodies without an anatomical structure engaging member; large sized J-shaped modular anatomical structure engaging member or head 87A, small sized J-shaped modular anatomical structure engaging member or head 87B, large fork-shaped modular anatomical structure engaging member or head 89A, small fork-shaped modular anatomical structure engaging member or head 89B, L-shaped modular anatomical structure engaging member or head 95A, or any combinations thereof.

Figure 35:
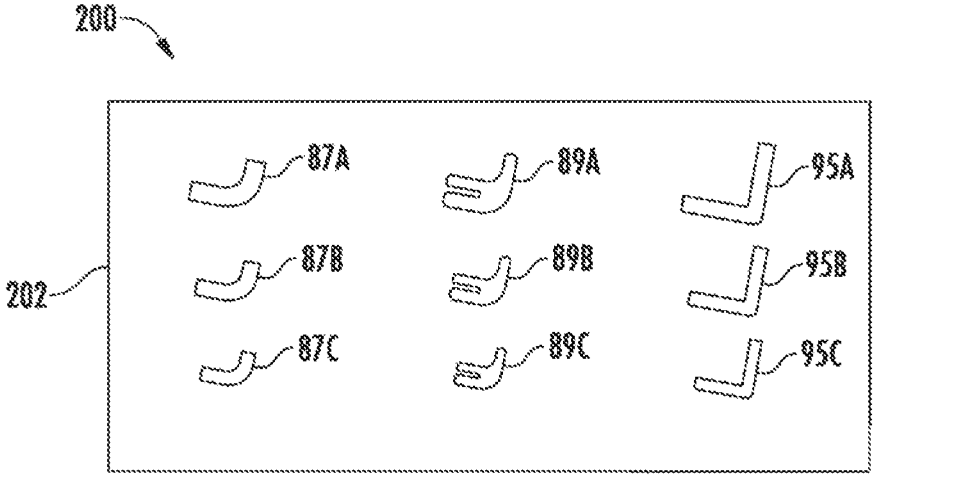
FIG. 35 illustrates a nerve retracting kit with anatomical structure engaging members and/or modular anatomical structure engaging members.
Figure 36:
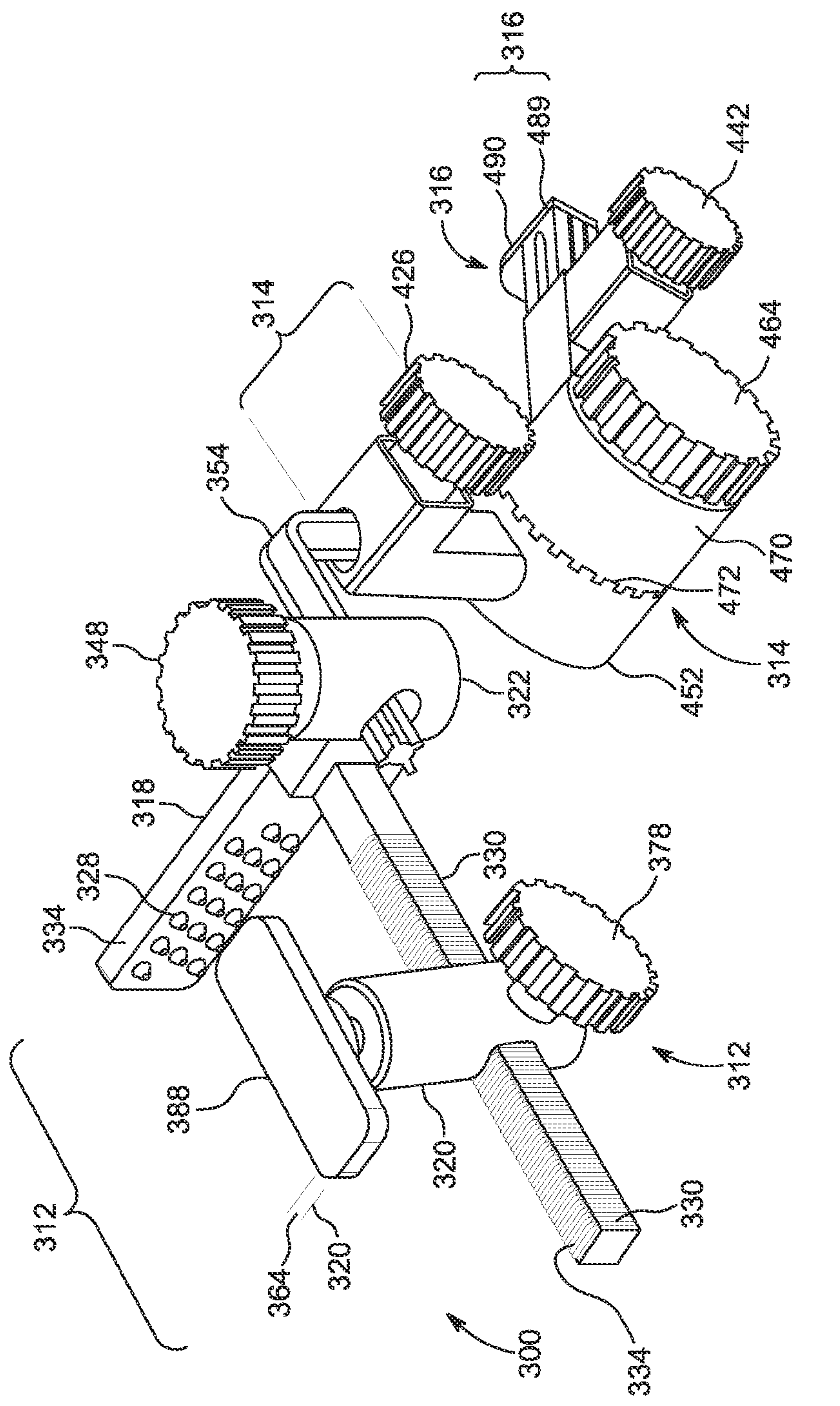
FIG. 36 is a perspective view of an alternative embodiment of the nerve retractor.
Figure 37:
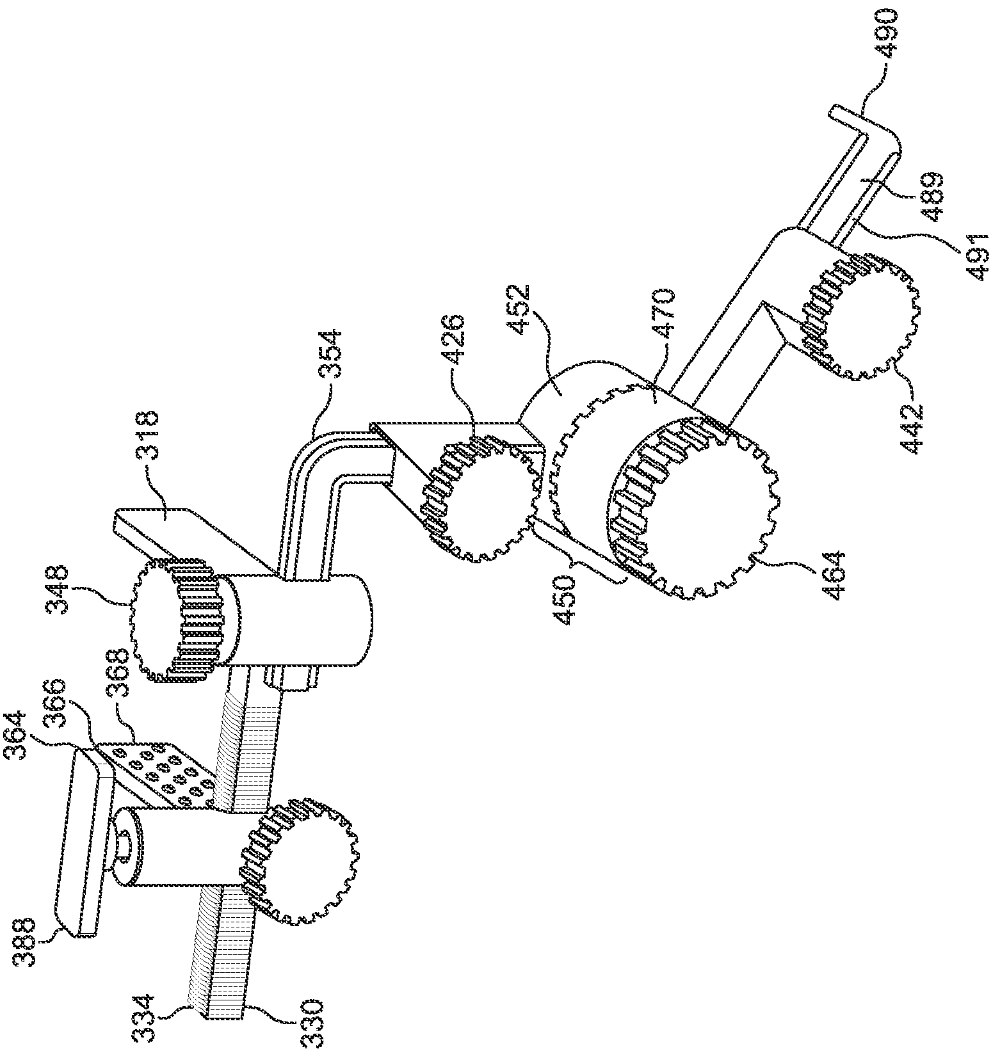
FIG. 37 is an alternative perspective view of the nerve retractor shown in FIG. 36.
Figure 38:
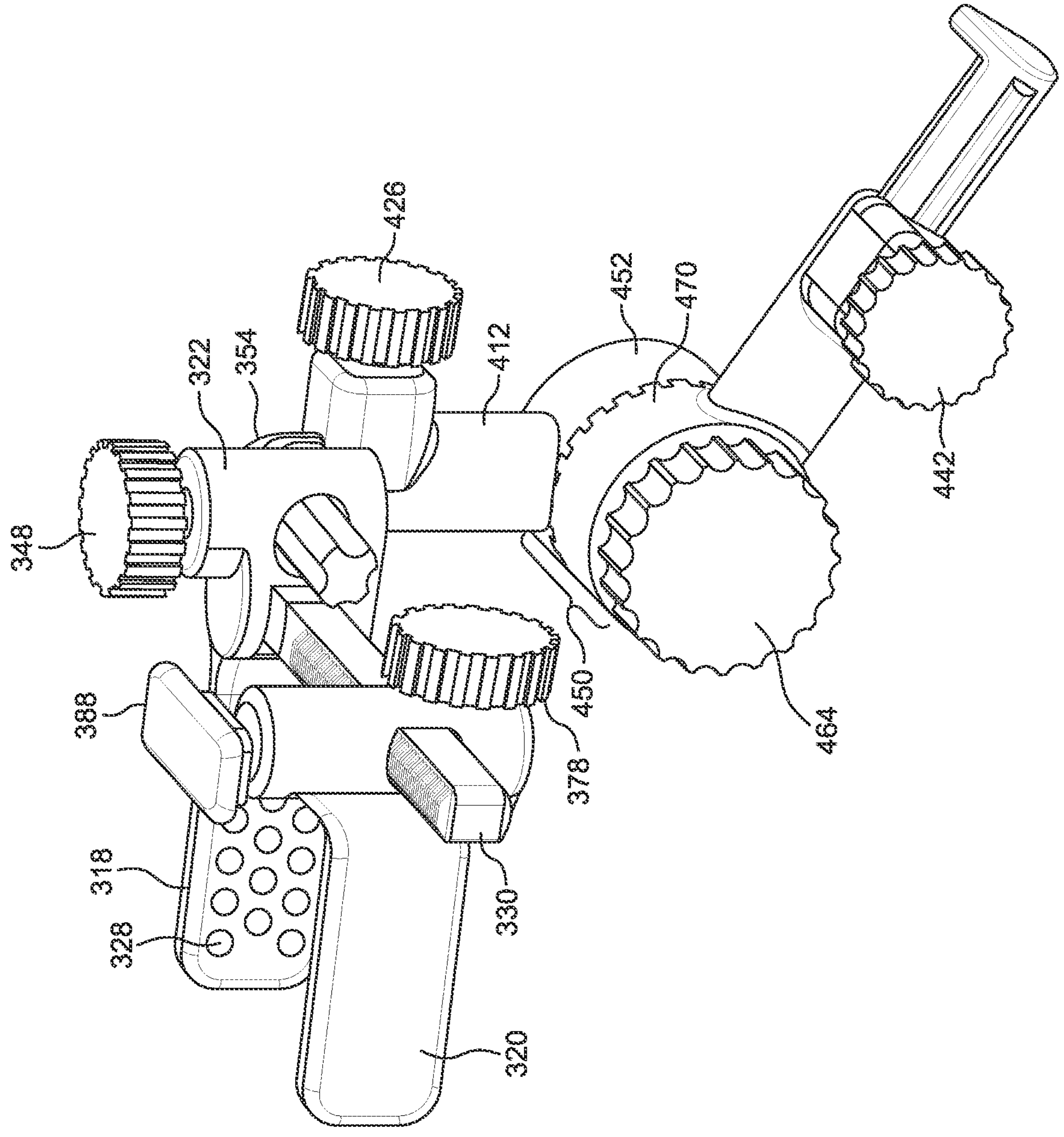
FIG. 38 is an alternative perspective view of the nerve retractor shown in FIG. 36.
Figure 39A:
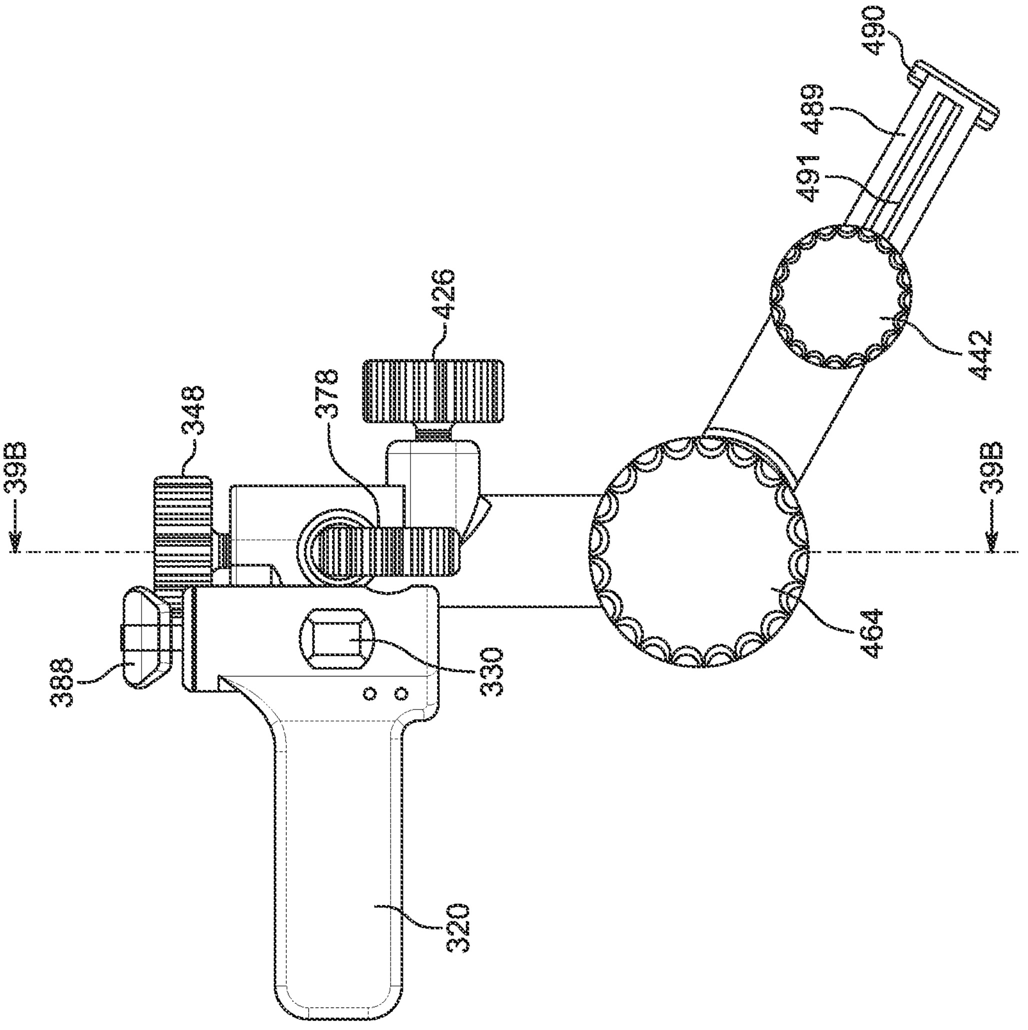
FIG. 39A is a side view of the nerve retractor shown in FIG. 36.
Figure 39B:
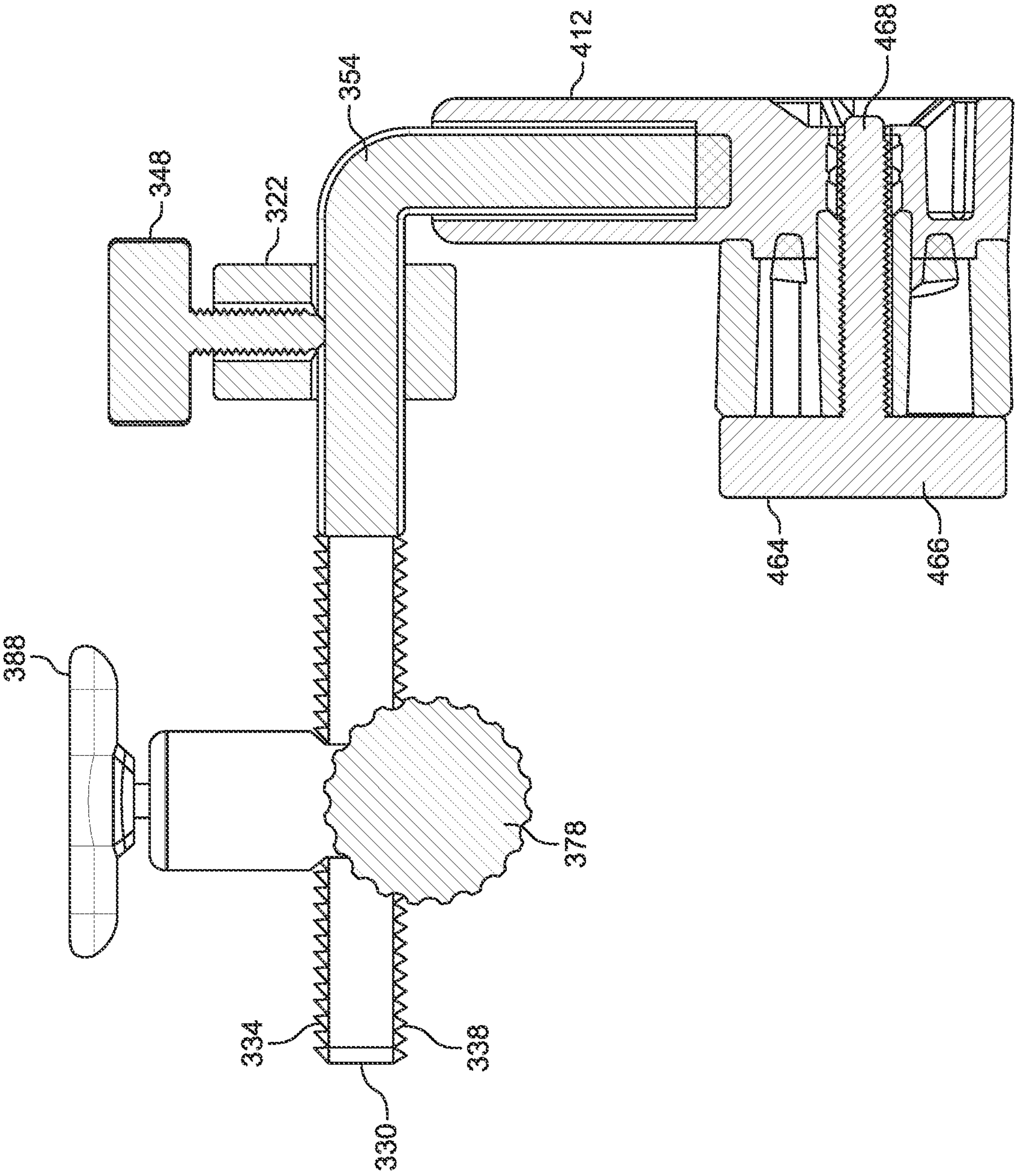
FIG. 39B is a cross sectional view of the nerve retractor taken along lines 39B-39B, in FIG. 39A.

FIG. 35 illustrates a nerve retractor kit 200 comprising a plurality of different shaped and sized modular anatomical structure engaging members or heads, including: large sized J-shaped modular anatomical structure engaging member or head 87A, medium sized J-shaped modular anatomical structure engaging member or head 87B, small sized J-shaped modular anatomical structure engaging member or head 87C, large sized fork-shaped modular anatomical structure engaging member or head 89A, medium sized fork-shaped modular anatomical structure engaging member or head 89B, small sized fork-shaped modular anatomical structure engaging member or head 89C, large L-shaped modular anatomical structure engaging member or head 95A, medium L-shaped modular anatomical structure engaging member or head 95B, small L-shaped modular anatomical structure engaging member or head 95C, or combinations thereof.

Referring to FIGS. 36-41, an alternative embodiment of the nerve retractor, referred to herein as nerve retractor 300 is shown. The nerve retractor 300 is similar to nerve retractor 10, differing mainly in the mechanism to secure to the part of the body, such as the spine. Similar to nerve retractor 10, the nerve retractor 300 is designed to allow a user, such as a surgeon, to steadily retract a spinal sac and nerve root traveling through the spinal canal. The nerve retractor 300 is designed to provide the user with an easier and safer tool to provide access to the surgical target, allowing the surgeon to work without damaging vital neural structures. The nerve retractor 300 is designed to eliminate the requirement of having an independent member hold the retractor tool, thus providing a safer procedure. Where applicable, functioning for the nerve retractor 10 described above may be applicable to one or more components of the nerve retractor 300.

The nerve retractor 300 comprises three components, an upper portion 312 (similar to base portion 12), a mid-portion 314 (similar to the arm portion 14) and a lower portion 316 (similar to the anatomical structure retractor portion 16). The upper portion 312 is configured to engage with or secure to at least a portion of an anatomical structure of an animal, such as a human spine, or a part of a surgical instrument. The mid-portion 314 is configured to provide an actuating mechanism for retractor angle adjustment. The lower portion 316 is configured to engage or interact with an anatomical structure, such as a nerve, moving it from its original location, out of the field where the user may need to operate or perform a procedure.

The upper portion 312 comprises an anatomical structure engaging or clamping member, which includes a rack body 318 and a clamping body 320. The rack body 318 comprises a main body 322, illustrated herein as a generally cylindrically shaped structure. An arm or finger like-projection 324 extends away from the rack body main body 322. An inner surface 326 contains one or more anatomical structure engaging members 328, illustrated herein as a plurality of spikes 328 arranged in rows. The spikes 328 are configured to secure to, by penetrating into, at least a portion of the anatomical structure. Extending from the rack body main body 322, shown in a generally perpendicular orientation relative to the arm or finger like projection 324, is a cross bar member 330, illustrated as an elongated bar or rod. The cross bar member 330 having a first surface 332 which includes a first set of ratchet teeth 334, and a second, opposing surface 336 having a second set of ratchet teeth 338, see FIG. 40B. The cross-bar member 330 may be integrally formed from the rack body main body 322, or may be an independent structure secured thereto.

The rack body main body 322 includes a first opening 340 positioned on upper surface 342 and a second opening 344 placed within the surface 346. The first opening 340 is sized and shaped to receive a position fixer 348 having a knob 350 and threaded body 352. The second opening 344 extends through the length of the rack body main body 322 to the other side, and is sized and shaped to receive and store within at least a portion of a connector rod 354. The connector rod 354 is configured to link the upper portion 312 and the mid-portion 314, and includes a first portion 356 which fits within the second opening 344 of the rack body main body 322, and a second portion 358 which is sized and shaped to engage with a portion of the mid-portion 314. The first portion 356 and the second portion 358 may be separated by a bent or curved portion 360. Turning the knob 350 in a clockwise/counter-clockwise direction locks or unlocks the connector rod 354 in place, or allows a user to change or re-position the rack body main body 322 on the connector rod 354. The connector rod 354 may include one or more cut outs or channels 355, preferably spanning the entire length. The one or more cut outs or channels 355 may be sized and shaped to receive a portion of a position fixer. Preferably the treaded rod portion.

The clamping body 320 comprises a main body 362, illustrated herein as a generally cylindrically shaped structure. A clamping body arm or finger-like projection 364 extends away from the clamping body main body 362. An inner surface 366 (see FIG. 37) contains one or more anatomical structure engaging members 368, illustrated herein as a plurality of spikes arranged in rows. The spikes 368 are configured to secure to, by penetrating into, at least a portion of an anatomical structure. The clamping body 320 is designed to move about the cross-bar member 330. Since the rack body main body 322 is fixed in position, moving the clamping body 320 about the cross-bar member 330 (preferably in a linear direction to the left or right, see arrow 370, FIG. 40A) expands or narrows the distance D or space separating the rack body arm or finger like-projection 324 and the clamping body arm or finger-like projection 364, see FIG. 40A.

The linear movement about the cross-bar member 330 may be accomplished using a ratchet mechanism. The clamping body main body 362 comprises a first body opening 372 extending through the length of the clamping body main body 362 to the other side, and is sized and shaped to receive and store within at least a portion of the connector rod 354, thus allowing the connector rod 354 to move within an interior 344 (see FIG. 40B). A second body opening 394 is sized and shaped to receive and hold within the interior 344 a ratchet gear 376 (and ratchet pinion pins 377); the ratchet gear 376 having a ratchet wheel 378 which allows a user to actuate the ratchet gear 376 by turning it in a clockwise or counter-clockwise direction. The ratchet gear 376 has teeth 380 that align and interact with the second set of ratchet teeth 338. A third opening 382 located at the upper end 384 of the clamping body main body 362 is sized and shaped to receive and hold therein a release mechanism 386.

The release mechanism 386, including a release handle 388, a ratchet locker 390, a spring 392, and a ratchet cap 396, is sized and shaped to fit within or over the third opening 382. The ratchet locker 390 may include an elongated body 398, illustrated herein as a rod, having a first end 400 and a second, opposing end 402. The first end is secured to or is integrally formed from the release handle 388. The second, opposing end 402 comprising a release/locking mechanism 404 designed to interact with the first set of ratchet teeth 334 of the cross-bar member 330.

The release/locking mechanism 404 comprises a release/locking engaging member 406, illustrated herein as a teeth engaging member having a body 408 with a pointed end 410. The pointed end 410 is sized and shaped to fit within or between two individual teeth of the first set of ratchet teeth 334 of the cross-bar member 330, thus preventing unwanted movement of the clamping body 320. In use, when a user moves the clamping body 320 to a sufficient distance relative to the rack body 318 by manipulating, i.e. rotating the ratchet gear 376, the user may apply a force (which may be a downward force or a turning force) to or against the release handle 388, the release/locking mechanism 404 engages with the first set of ratchet teeth 334 of the cross-bar member 330, preventing further movement of the clamping body 320. To release this position, the user simply applies another force or turns the release handle in an opposite direction, thus removing the pointed end 410 positioned within or between two individual teeth of the first set of ratchet teeth 334 of the cross-bar member 330.

The mid-portion 314 is designed to provide stepped, angular positioning of the lower portion 316. The mid-portion 314 comprises a retractor angle adjuster first or bottom portion 412 and a retractor angle adjuster second or top portion 414 (similar to arm 14 described for retractor 10). The retractor angle adjuster first or bottom portion 412 comprises a main body 416, illustrated herein as an elongated, tubular shaped object having a first end 418 and a second, opposing end 420; the first end 418 having an opening 422 sized and shaped to receive and hold therein at least a portion of the connector rod 354 (such as connector rod second portion 358). A second opening 424 is sized and shaped to receive and hold therein a position fixer 426 having a knob 428 and threaded body 430. The position fixer 426 maintains (or allows adjustment of) the positioning of the connector rod 354 portion inserted into the retractor angle adjuster first or bottom portion 412. Secured to or integrally formed to the second, opposing end 420 is a first member of a retractor actuating unit 432, (also referred to as first retractor actuating member 432).

The retractor angle adjuster upper portion 414 includes a main body 434, illustrated herein as an elongated, tubular shaped object having a first end 436 and a second, opposing end 437. Attached to, or integrally formed to, the first end 436 is a second member of a retractor actuating unit 438 (also referred to as a second retractor actuating member 438). The second, opposing end 437 comprises a first opening 440, sized and shaped to receive and hold therein a position fixer 442 having a knob 444 and threaded body 446. The position fixer 442 maintains (or allows adjustment of) the positioning of the lower portion 316 when at least a portion thereof is inserted within the bottom surface opening 448.

The first retractor actuating member 432 is configured to interact with the second retractor actuating member 438. The second retractor actuating member 438 is configured to interact with the first retractor actuating member 432. Together, the first retractor actuating member 432 and the second retractor actuating member 438 form the retractor actuator 450 (same as the retractor actuator 68 of nerve retractor 10). The retractor actuator 450 is designed and functions to move and set the retractor angle adjuster second or top portion 414 at various angles. Moving and setting the retractor angle adjuster second or top portion 414 at various angles allows the lower portion 316 to be moved and set at different angles as well, allowing the surgeon to retract a nerve root as far back as needed.

Figure 40A:
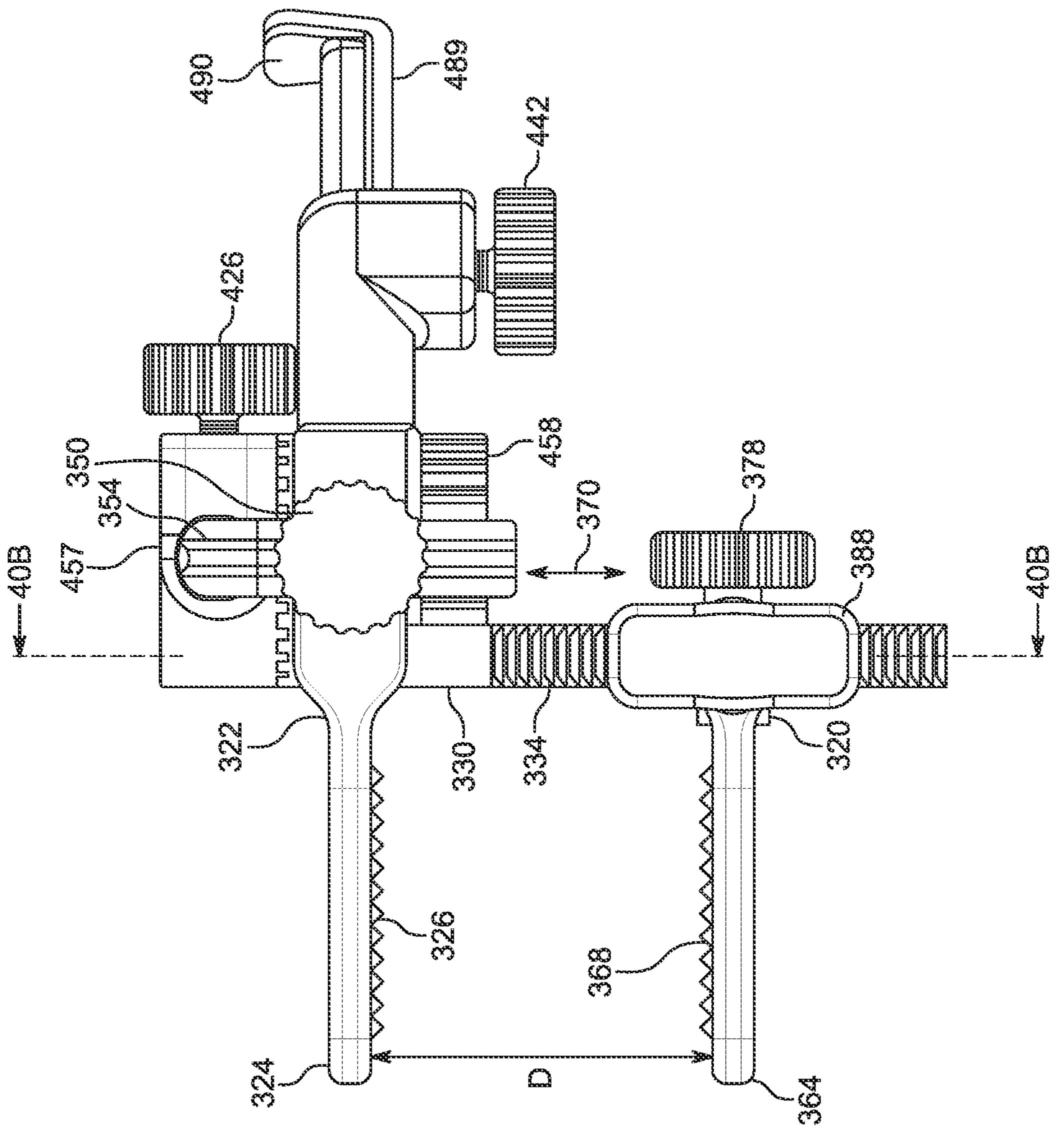
FIG. 40A is a top view of the nerve retractor shown in FIG. 36.
Figure 40B:
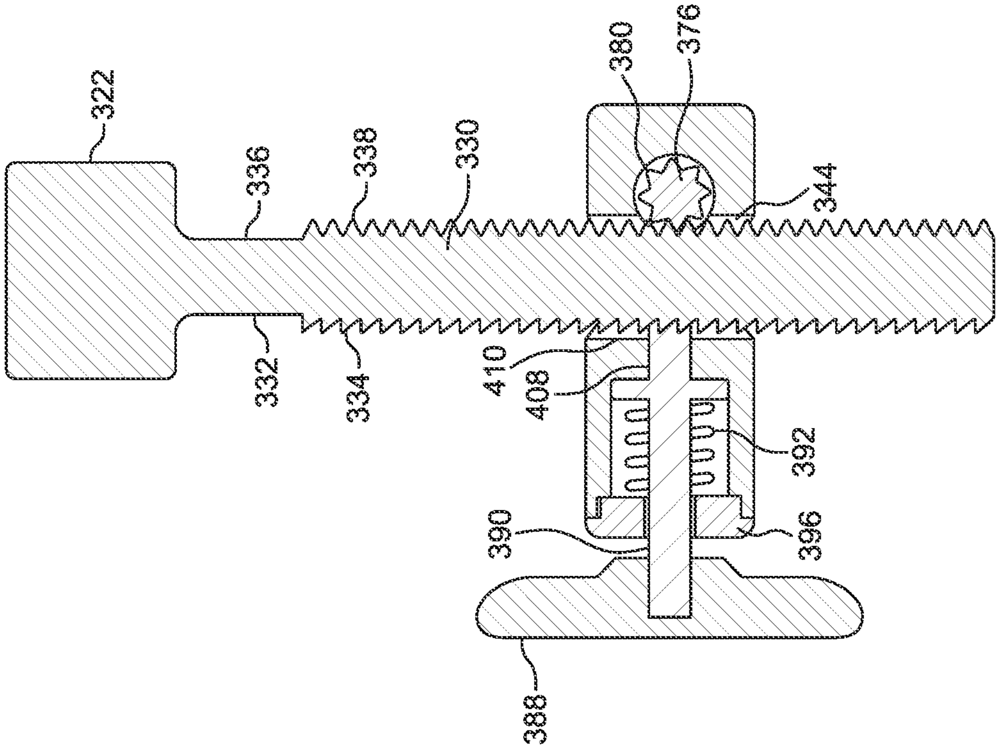
FIG. 40B is a cross sectional view of the nerve retractor taken along lines 40B-40B in FIG. 40A.

The first retractor actuating member 432 is illustrated as a circular or wheel shaped body 452 having an inner surface 456 (FIG. 41) and an outer surface 458 (FIG. 40A). The outer surface 457 preferably has a generally planar and smooth surface. The inner surface 456 has a plurality of teeth 458 (may also be referred to as first teeth 458 or first retractor actuating member teeth 458) and gaps 460, circumferentially arranged and spaced apart. Each of the plurality of teeth 458 are sized, shaped and arranged to engage or interconnect with a second set of teeth (to be described later) associated with the second retractor actuating member 438. The first retractor actuating member 432 may contain an opening 462, preferably with threading 463 (and optionally a steel insert 465), to engage and secure with a retractor angle adjuster 464. The retractor angle adjuster 464 includes a knob 466 and threaded body 468 extending away from the knob 466 which secures to threading 463.

Figure 41:
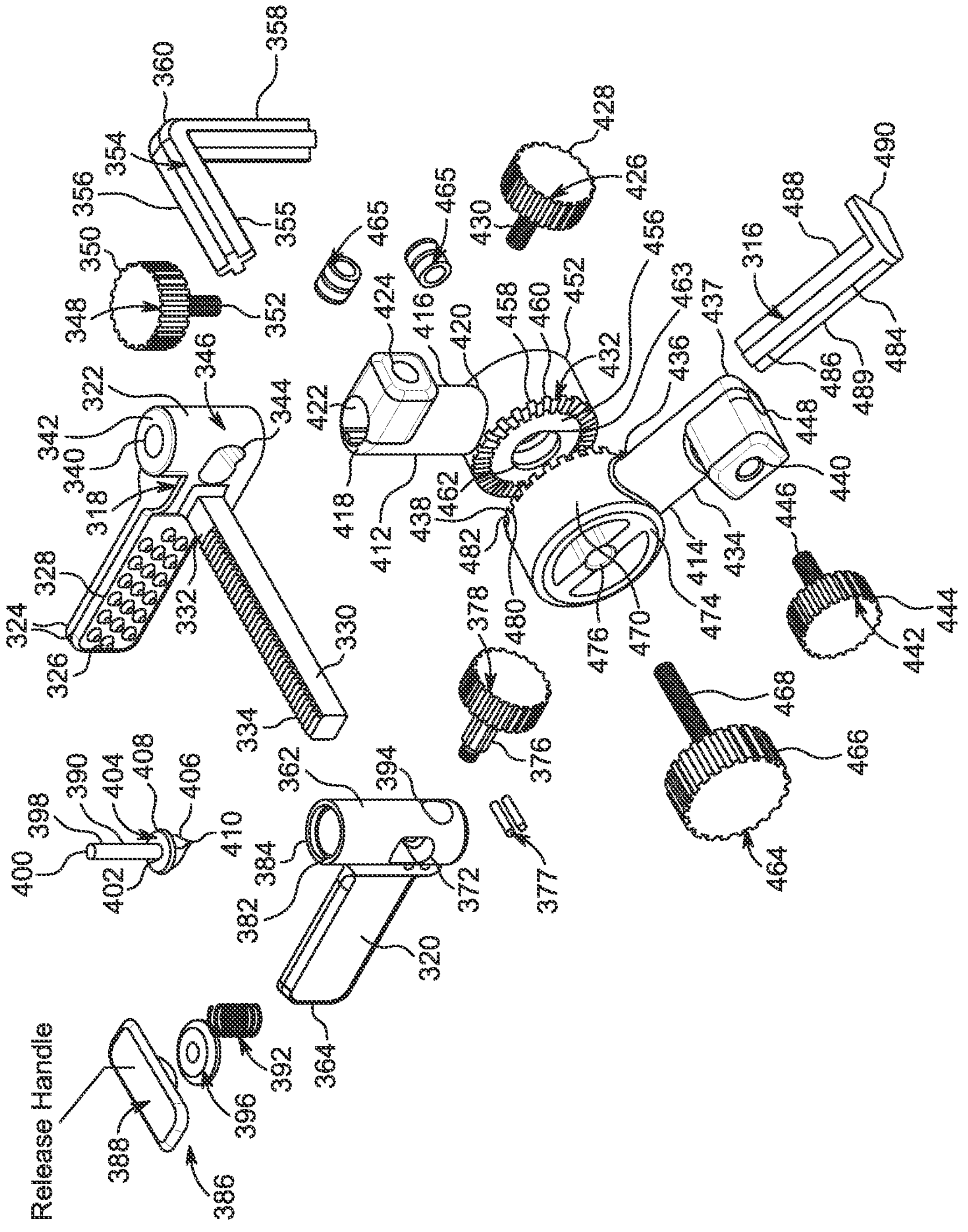
FIG. 41 is an exploded view of the nerve retractor shown in FIG. 36.

The second retractor actuating member 438 is illustrated as a circular or wheel shaped body 470 having an inner surface 472 (FIG. 36) and an outer surface 474 (FIG. 41). The outer surface 474 may contain an opening 476 sized and shaped to receive and hold the threaded body 468 of the retractor angle adjuster 464. The inner surface 472 has a plurality of teeth 480 (may also be referred to as second teeth 480 or second retractor actuating member teeth 480) and gaps 482, circumferentially arranged and spaced apart. Each of the plurality of teeth 480 and gaps 482 are sized, shaped and arranged to engage or interconnect with the first set of teeth 458 and gaps 460 associated with the first retractor actuating member 432. The retractor angle adjuster 464 allows a user to adjust the angle of the lower portion 316 by rotating the knob 466, causing the rotation of the first retractor actuating member 432 or the second retractor actuating member 438.

The nerve retractor lower portion 316 includes an anatomical structure retractor 484 (same as the anatomical structure retractor 16). The anatomical structure retractor 484 may be attached to, or integrally formed from, the retractor angle adjuster upper portion main body 434. Preferably, the anatomical structure retractor 484 extends from and away from the second, opposing end 437 of the retractor angle adjuster upper portion main body 434. The anatomical structure retractor 484 comprises a first end 486 (may also be referred to as a top end), an opposing second end 488 (may also be referred to as a bottom end), and a main body 489 therebetween. The connector main body 489 may include one or more cut outs or channels 491 (FIG. 39A), preferably spanning the entire length. The one or more cut outs or channels 491 may be sized and shaped to receive a portion of a position fixer. Preferably the treaded rod portion. The anatomical structure retractor first end 486 is configured to connect with or to a portion of the retractor angle adjuster second or top portion 414 includes a main body 434, i.e. within opening 448. The second end 488 of the anatomical structure retractor second end 484 comprises an anatomical structure engaging member 490, illustrated herein as a body extending out in a generally perpendicular orientation from the main body 489, forming a J- or L-shaped hooked end. While shown having a J- or L-shaped hooked end, the anatomical structure engaging member 490 may have any shapes, embodiments, or functions as that described for the anatomical structure retractor 16, including being modular.

Figure 42:
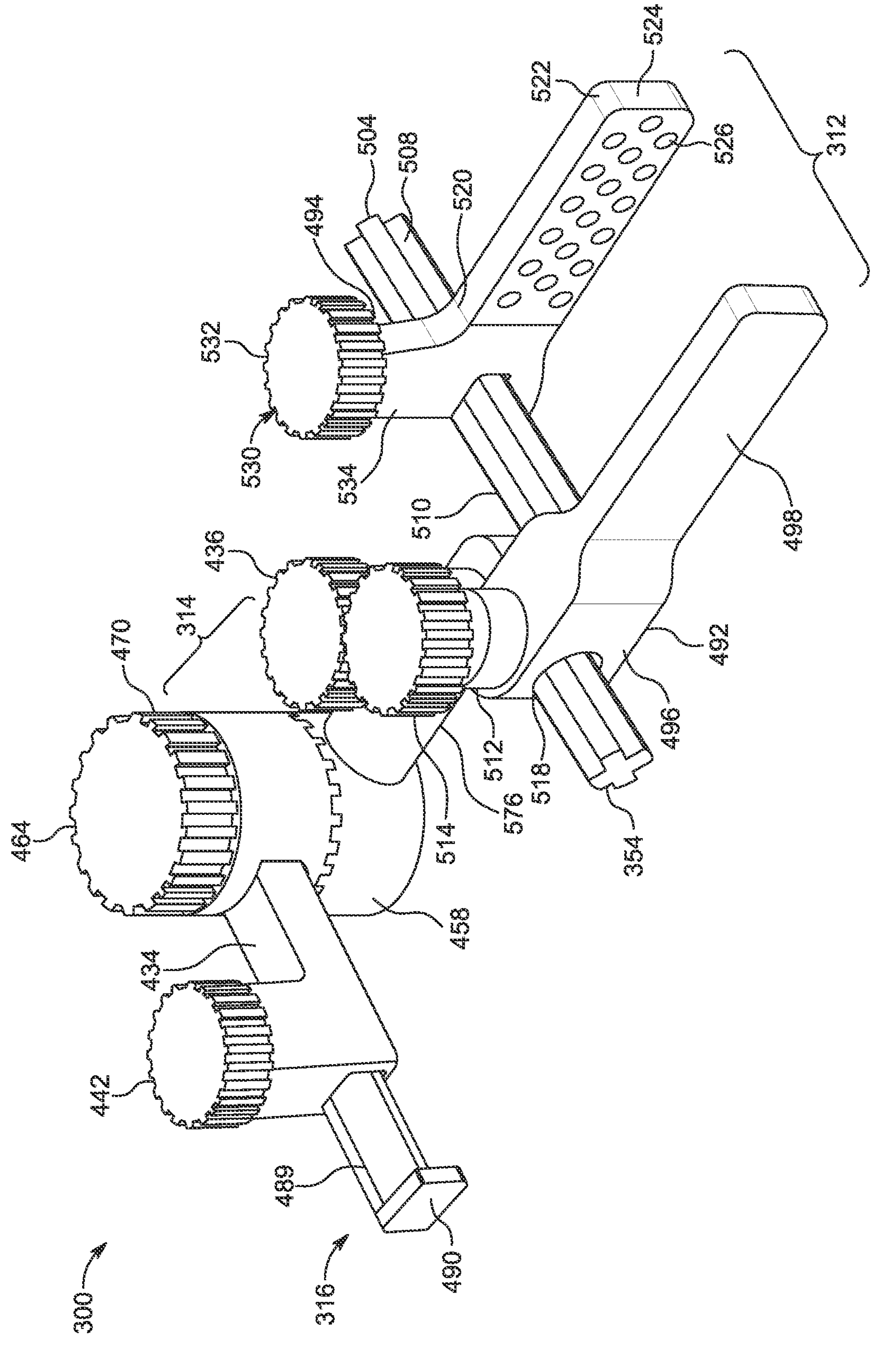
FIG. 42 is a perspective view of an alternative embodiment of the nerve retractor.
Figure 43:
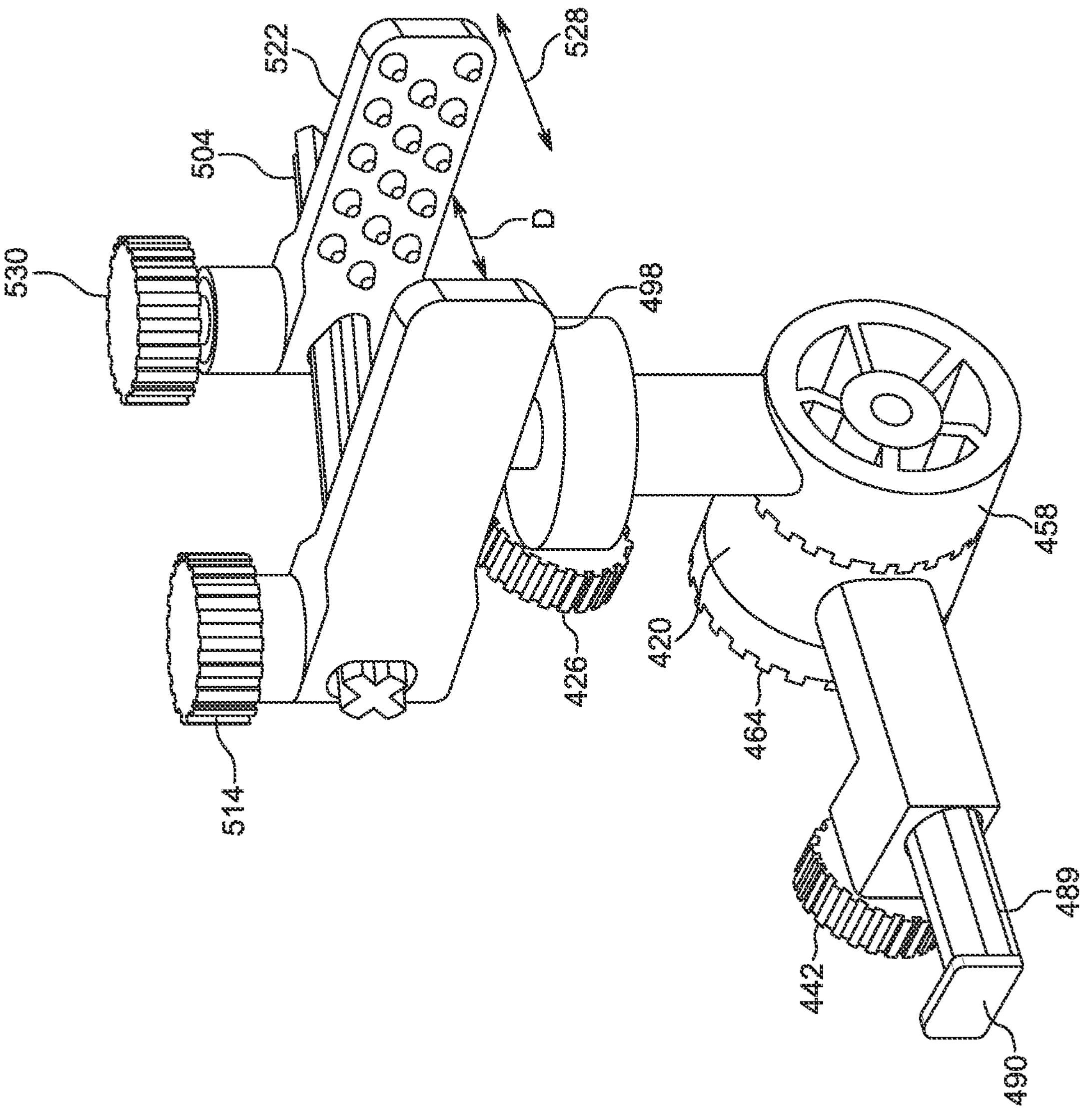
FIG. 43 is a front perspective view of the nerve retractor shown in FIG. 42.
Figure 44:
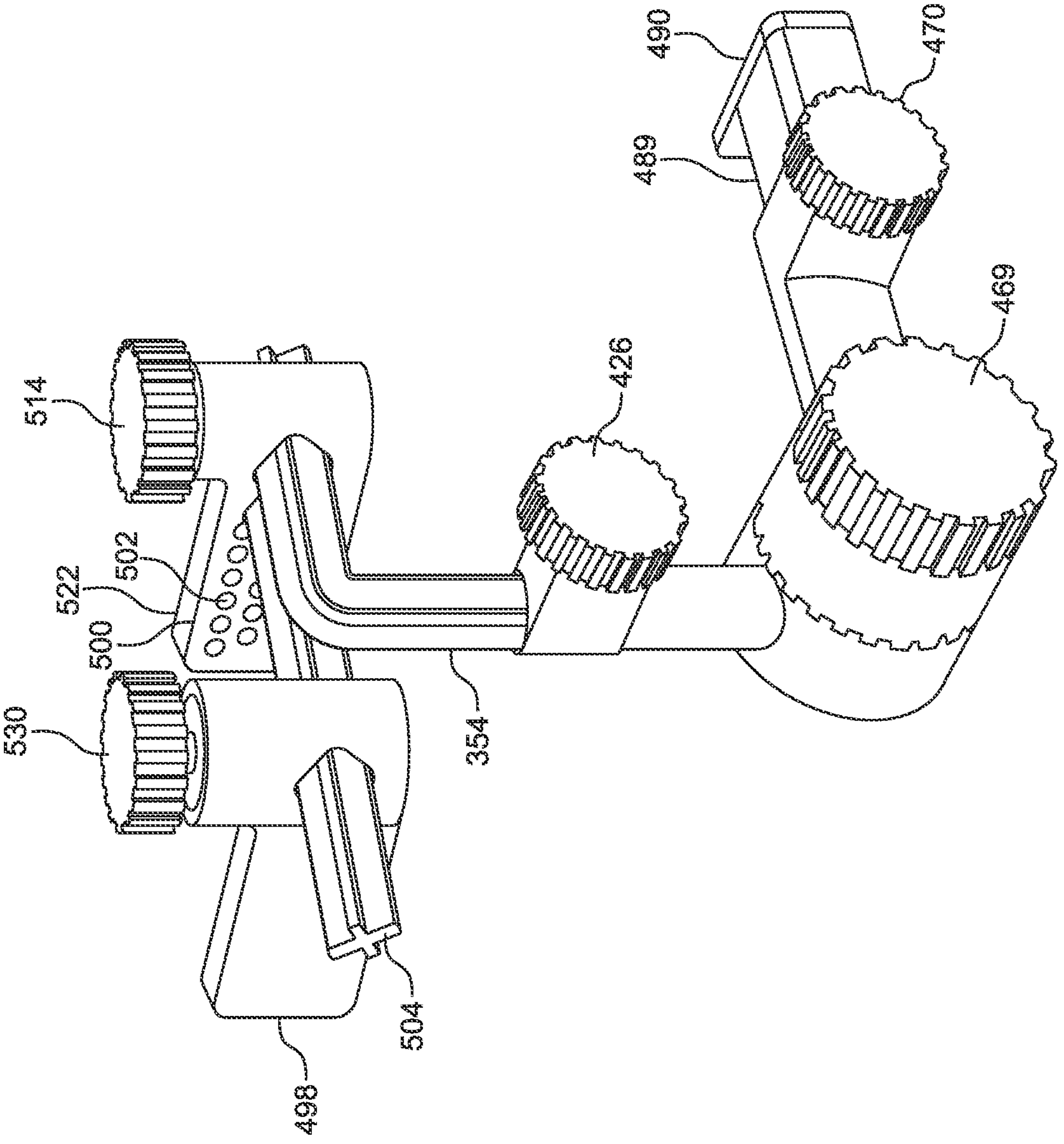
FIG. 44 is a back perspective view of the nerve retractor shown in FIG. 42.

Referring to FIGS. 42-44, an alternative embodiment of the nerve retractor 300 is shown; the nerve retractor shown in FIGS. 42-45 differing in that it contains an alternative embodiment of the upper portion 312. The mid portion 314 and the lower portion 316 have the same structures and features. The upper portion 312 of the embodiment shown in FIGS. 42-45 comprises an anatomical structure engaging or clamping member which includes a rack body 492 and a clamping body 494. The rack body 492 comprises a main body 496, illustrated herein as a cylindrically shaped structure. An arm or finger like-projection 498 extends away from the rack body main body 496. An inner surface 500, see FIG. 44, contains one or more structure (such as an anatomical structure or surgical instruments, such as retractors) engaging members 502, illustrated herein as a plurality of spikes arranged in rows. The structure engaging members 502 are configured to secure to, by penetrating into, at least a portion of an anatomical structure. While illustrated as structures that penetrate into another structure, the structure engaging members 502 may be configured to attach to surfaces in other ways, such as but not limited to forming curvilinear features which fit within the curvilinear features of a retractor blade. Extending from rack body main body 492, shown in a generally perpendicular orientation relative to the arm or finger like projection 498, is a cross bar member 504, illustrated as an elongated bar or rod. The cross-bar member 504 may be integrally formed from the rack body main body 496, or may be an independent structure secured thereto. The cross bar 504 has a surface 508 which includes one or more cut outs or channels 510, preferably spanning the entire length.

The rack body main body 496 includes a first opening 512 sized and shaped to receive a position fixer 514 having a knob 516 and threaded body (not illustrated). A second opening 518 extends through the length of the rack body main body 496 to the other side, and is sized and shaped to receive and store within at least a portion of a connector rod 354.

The clamping body 494 comprises a main body 520, illustrated herein as a generally cylindrically shaped structure. A clamping body arm or finger-like projection 522 extends away from the clamping body main body 520. An inner surface 524 (see FIG. 42) contains one or more structure (such as an anatomical structure or surgical instruments, such as retractors) engaging members 526, illustrated herein as a plurality of spikes arranged in rows. The one or more structure engaging members 526 are configured to secure to, by penetrating into, at least a portion of an anatomical structure. While illustrated as structures that penetrate into another structure, the one or more structure engaging members 526 may be configured to attach to surfaces in other ways, such as but not limited to forming curvilinear features which fit within the curvilinear features of a retractor blade. The clamping body 494 is designed to move about the cross-bar member 504. Since the rack body main body 496 is fixed in position, moving the clamping body 494 about the cross-bar member 504 (preferably in a linear direction to the left or right, see arrow 528, FIG. 43) expands or narrows the distance D or spaced separating the rack body armor finger like-projection 498 and the clamping body arm or finger-like projection 522.

The one or more cut outs or channels 510 may be sized and shaped to receive a portion of a position fixer 530; the position fixer 530 having a knob 532 and threaded body (not shown), with the threaded body fitting tightly within the one or more cut outs or channels 510 (in the locked position) when inserted within an opening 534. In the unlocked position, the clamping body arm or finger-like projection 522 can be moved left or right by application of an applied force.

Figure 45:
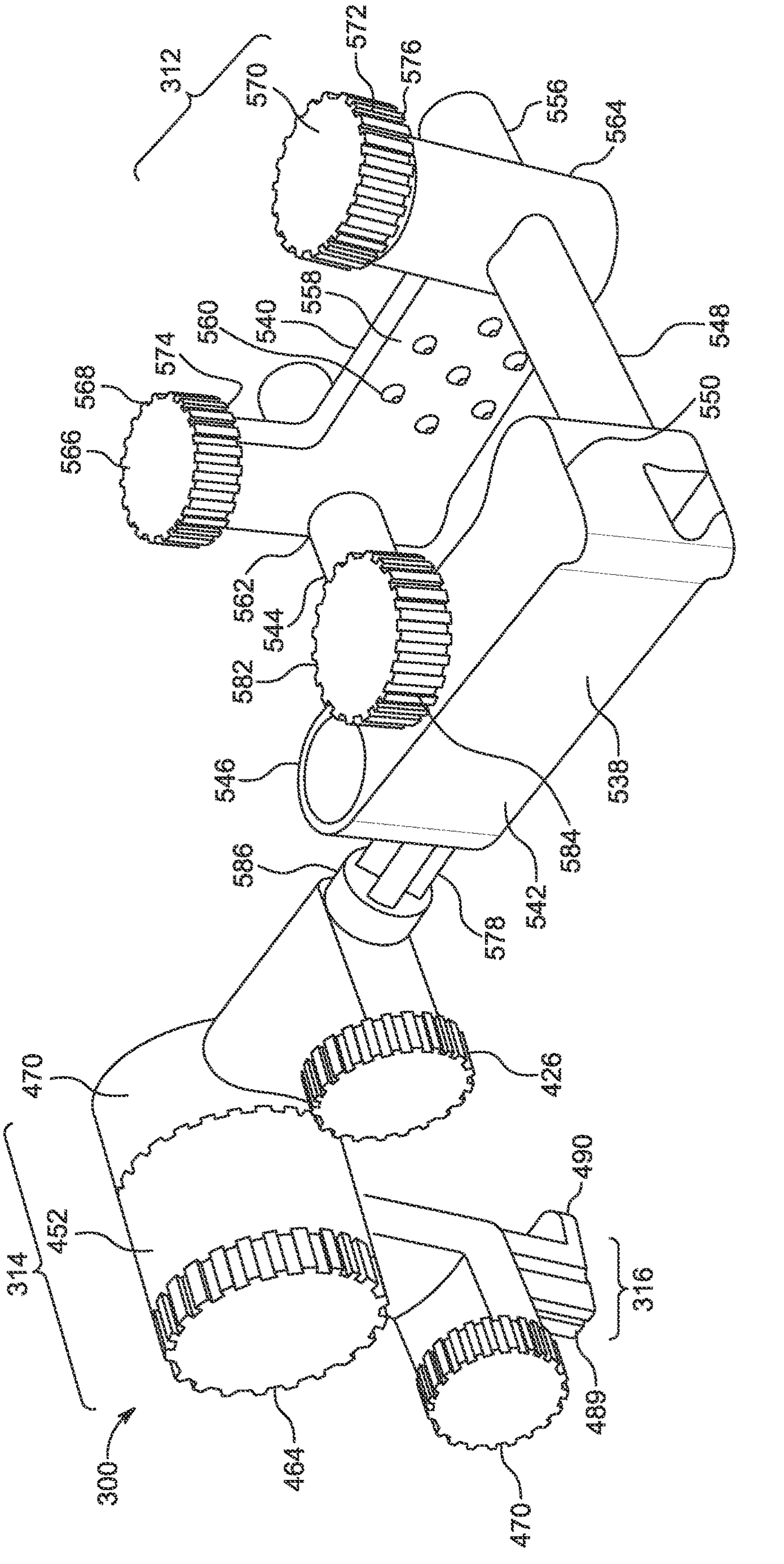
FIG. 45 is a perspective view of an alternative embodiment of the nerve retractor.
Figure 46:
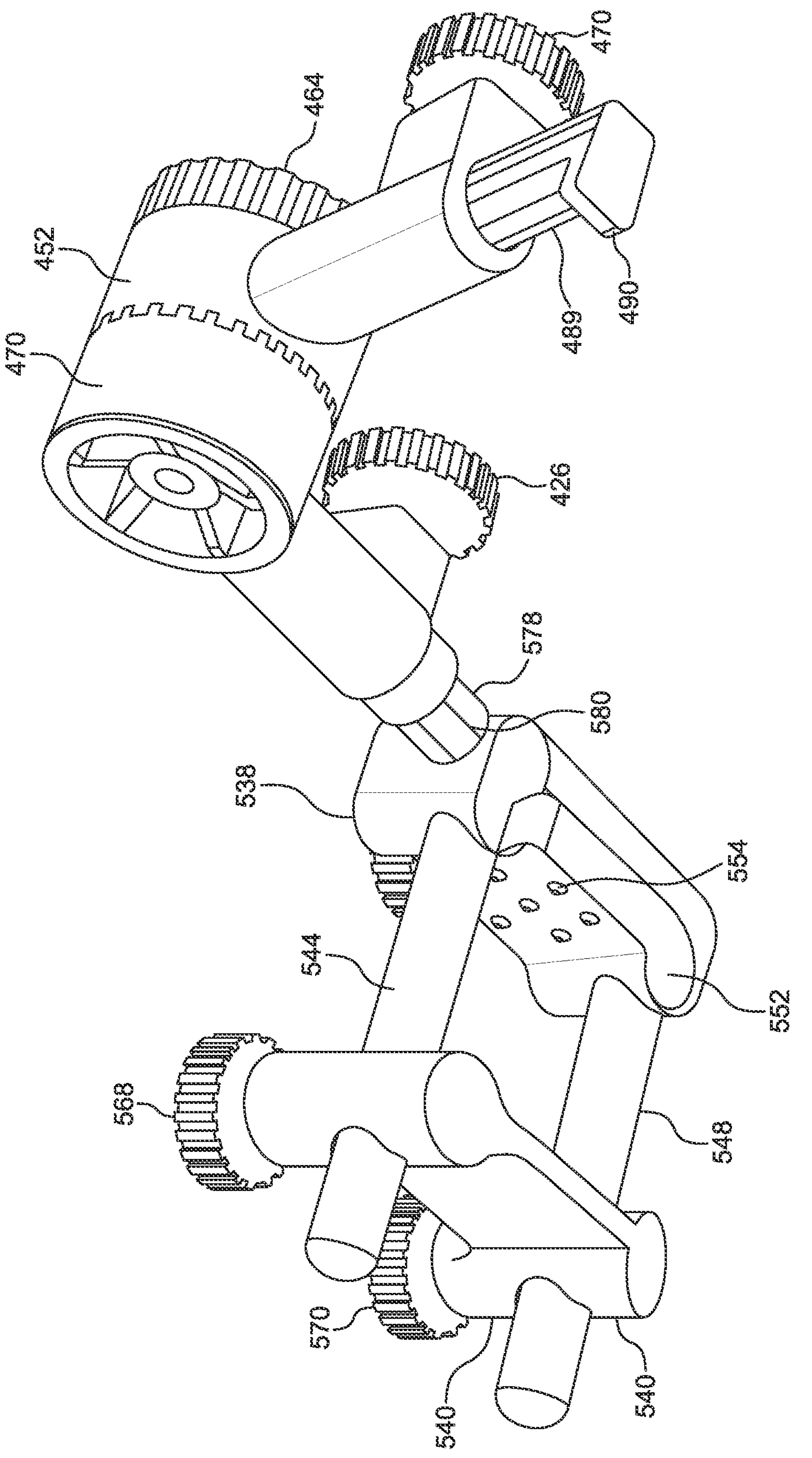
FIG. 46 is an alternative perspective view of the nerve retractor shown in FIG. 45.

Referring to FIGS. 45-46, an alternative embodiment of the nerve retractor 300 is shown; the nerve retractor 300 shown in FIGS. 45-46 differing in that it contains an alternative embodiment of the upper portion 312. The mid portion 314 and the lower portion 316 have the same structures and features. The upper portion 312 of the embodiment shown in FIGS. 45-46 comprises an anatomical structure engaging or clamping member which includes a rack body 538 and a clamping body 540. The rack body 538 comprises a main body 552, illustrated herein as an elongated, rectangular shaped structure. The rack body main body 552 comprises a first arm or finger like-projection 544 positioned at a first end 546 and a second arm or finger like-projection 548 positioned at a second end 550. The first arm or finger like-projection 544 and the second arm or finger like-projection 548 may be integrally formed from the rack body main body 538, or may be an independent structure secured thereto.

The first arm or finger like-projection 544 and the second arm or finger like-projection 548 extend away from the rack body main body 552, and are arranged in a parallel orientation relative to each other and spaced apart. An inner surface 500 of the rack body 538, see FIG. 46, contains one or more structure (such as an anatomical structure or surgical instruments) engaging members 554, illustrated herein as a plurality of spikes arranged in rows. The one or more structure engaging members 554 are configured to secure to, by penetrating into, at least a portion of an anatomical structure or other surgical instruments, such as retractor systems or retractor blades. While illustrated as structures that penetrate into another structure, the one or more structure engaging members 554 may be configured to attach to surfaces in other ways, such as but not limited to forming curvilinear features which fit within the curvilinear features of a retractor blade.

The clamping body 540 comprises a main body 556, illustrated herein as an elongated, rectangular shaped structure. An inner surface 558 of the clamping body 540, see FIG. 45, contains one or more structure (anatomical structure or surgical instruments such as retractors) engaging members 560, illustrated herein as a plurality of spikes 560 arranged in rows. The one or more structure engaging members 560 are configured to secure to, by penetrating into, at least a portion of an anatomical structure. While illustrated as structures that penetrate into another structure, the one or more structure engaging members 560 may be configured to attach to surfaces in other ways, such as but not limited to forming curvilinear features which fit within the curvilinear features of a retractor blade. A first opening 562 and a second opening 564 are each sized and shaped to receive and hold therein at least a portion of the first arm or finger like-projection 544 and the second arm or finger like-projection 548, respectively. This arrangement allows the clamping body 540 to be moved linearly left or right, positioning the clamping body 540 closer or farther away from the rack body 538. A first position fixer 566 having a knob 568 and threaded body (not illustrated), and a second fixer 570 having a knob 572 and threaded body (not illustrated) are inserted into openings 574 and 576. The position fixers 566 and 570 maintain (or allow adjustment of) the positioning of the clamping body 540. The rack body 538 is linked to the mid-portion 314 via a connector rod 578. The connector rod 578 is inserted into opening 580. The opening 580 extends through the length of the rack body 538 to the other side. A position fixer 582 having a knob 584 and threaded body (not illustrated) fixes the positioning of the rack body 538 about the connector rod 578. The connector rod 578 may include channels or cut outs 586 sized and shaped to receive and hold therein the position fixer threaded body.

Figure 47:
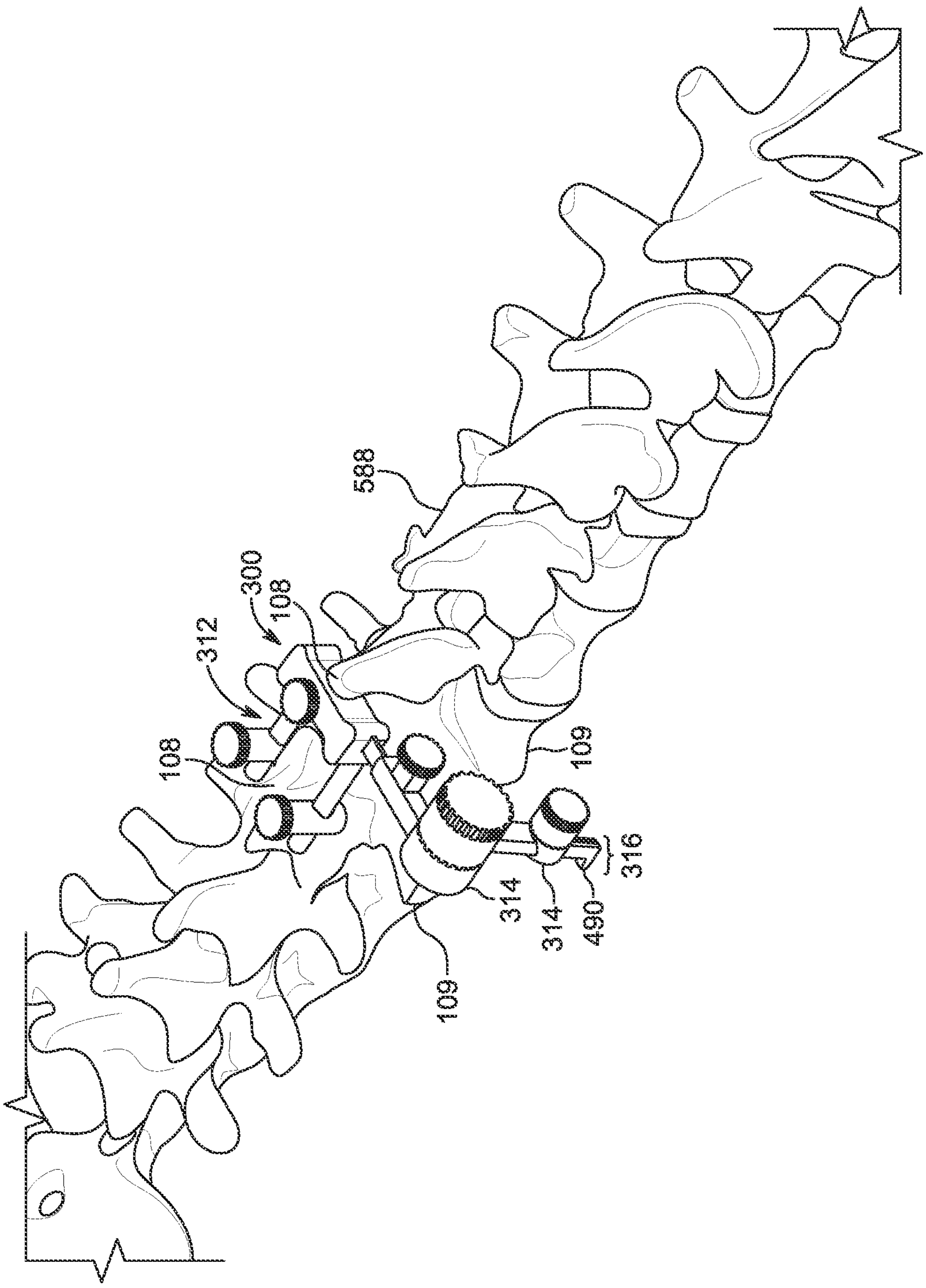
FIG. 47 illustrates the nerve retractor shown in FIG. 45 secured to a portion of the spine.
Figure 48:
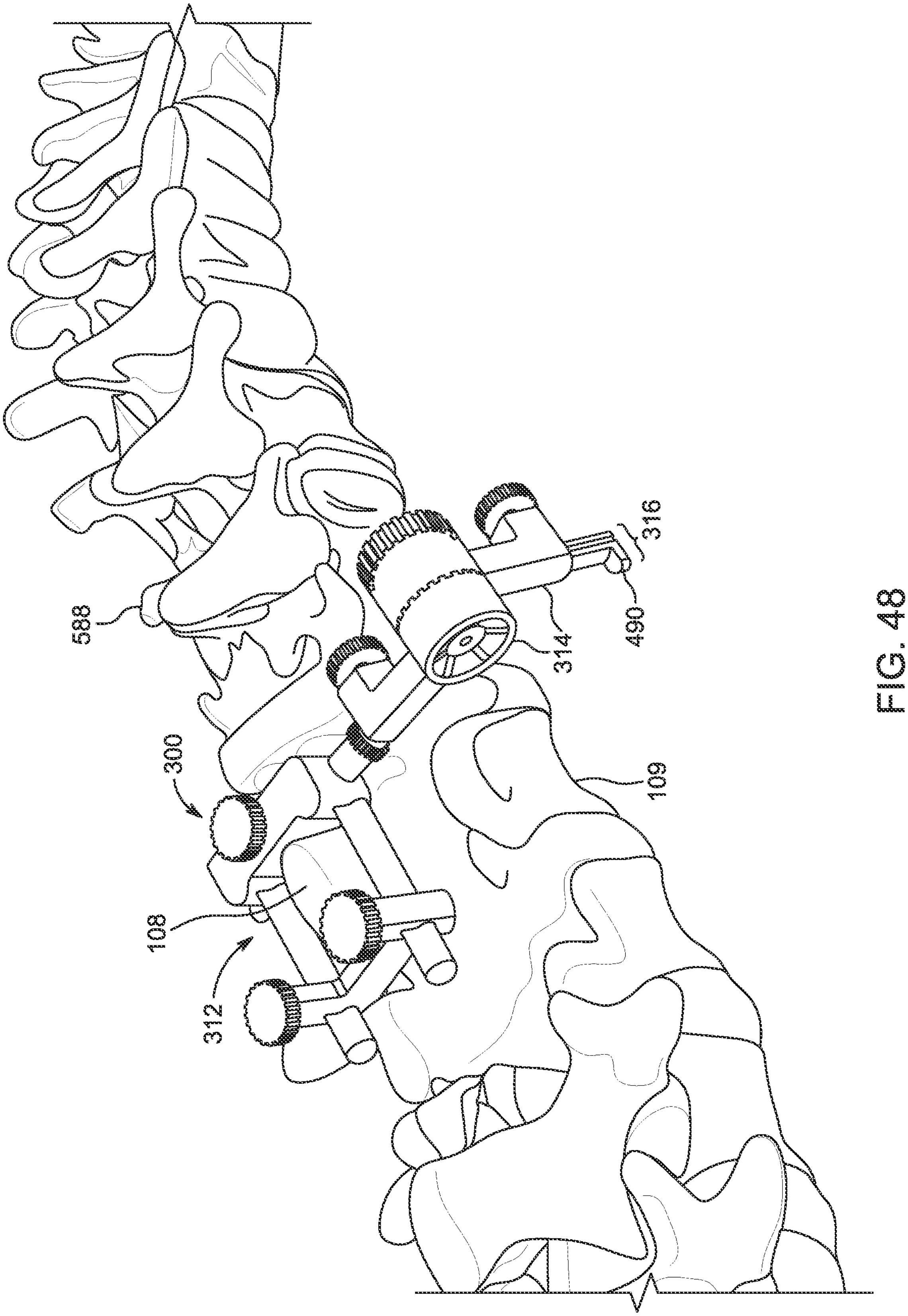
FIG. 48 is an alternative view of the nerve retractor shown in FIG. 45 secured to a portion of the spine.

FIGS. 47 and 48 illustrate the embodiment of the nerve retractor 300 shown in FIGS. 45-46 secured to a portion of the spine 588. Rather than attaching directly to the spinous process 108 as shown in FIG. 29 (associated with the embodiment of the nerve retractor 10), the nerve retractor 300, regardless of the embodiment described in FIGS. 36-46, is configured to engage with the spinous process 108 in a clamping mechanism. In the embodiment illustrated in FIGS. 47 and 48, the rack body 538 and a clamping body 540 are positioned in the front and back side of the spinous process 108, or other structures (such as metal surgical instruments), rather than being secured directly thereto by a screw. The connector rod 578 allows placement of the mid-portion 314 and the lower portion 316 at a distance away from the vertebra 109, allowing the anatomical structure engaging member 490 to be positioned for access to the spinal nerve.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A nerve retractor comprising:

a fastener configured to secure the nerve retractor to an anchor point;

a retractor that includes an anatomic structure engaging member; and a retractor actuator connecting the retractor to the fastener, wherein:

the retractor actuator is connected to the fastener by a connector rod, the connector rod includes a first elongated section and a second elongated section, the fastener is slidably connected to the first elongated section, the retractor actuator is slidably connected to the second elongated section, and the retractor actuator includes a rotatable interface configured to rotate the anatomic structure engaging member from a first position to a second position;

said fastener comprising a fastener body, a first clamping member, a second opposing clamping member, and a lock that releasably secures the fastener body to the first elongated section, wherein said fastener body defining a channel sized to receive the first elongated section; said first clamping member is fixedly attached to the fastener body, and said second clamping member is movably engaged to a crossbar extending from the fastener body.

2. The nerve retractor of claim 1, wherein the lock comprises:

a knob connected to a threaded barrel configured to be received by a threaded channel disposed within the fastener body, wherein a twisting force exerted on the knob causes the threaded barrel to mate with the threaded channel until the threaded barrel engages the first elongated section to secure the fastener body to the connector rod.

3. The nerve retractor of claim 1, wherein:

the first clamping member comprises one or more clamping member surface anatomical structure engaging members, and the second clamping member comprises one or more clamping member surface anatomical structure engaging members.

4. The nerve retractor of claim 1, wherein:

the crossbar includes a plurality of ratchet teeth, and the second clamping member further comprises a ratchet wheel configured to turn a ratchet gear that engages the plurality of ratchet teeth to move the second clamping member along the crossbar.

5. The nerve retractor of claim 4, further comprising:

a locking pin that selectively engages the plurality of ratchet teeth of the crossbar.

6. The nerve retractor of claim 5, wherein the locking pin further comprises:

a spring that biases the locking pin with a spring force to engage the plurality of ratchet teeth; and a handle configured to receive a lifting force that overcomes the spring force to disengage the locking pin from the plurality of ratchet teeth.

7. A nerve retractor, comprising:

a fastener configured to secure the nerve retractor to an anchor point;

a retractor comprising an anatomic structure engaging member disposed at an end of an elongated body; and a retractor actuator connecting the retractor to the fastener, wherein:

the retractor actuator is connected to the fastener by a connector rod, the connector rod includes a first elongated section and a second elongated section, the fastener is slidably connected to the first elongated section, the retractor actuator is slidably connected to the second elongated section, and the retractor actuator includes a rotatable interface configured to rotate the anatomic structure engaging member from a first position to a second position, wherein, the retractor actuator includes a first connector body connected to a first rotatable body and a second connector body connected to a second rotatable body;

the first connector body defines a first channel sized to receive the second elongate section;

the second connector body defines a second channel sized to receive the elongated body of the retractor; and the rotatable interface is disposed between the first rotatable body and the second rotatable body.

8. The nerve retractor of claim 7, wherein: the retractor actuator includes a first lock that releasably secures the second elongate section of the angled connector rod within the first connector body; and the retractor actuator includes a second lock that releasably secures the retractor within the second connector body.

9. The nerve retractor of claim 7, wherein the rotatable interface comprises a plurality of interlocking teeth configured to provide a stepped rotation of the first rotatable body relative to the second rotatable body.

10. The nerve retractor of claim 9, further comprising:

a lock that removably secures the first rotatable body with the second rotatable body.

11. The nerve retractor of claim 1, wherein the first elongated section is angled relative to the second elongated section.

* * * * *